(12) United States Patent
Hon

(10) Patent No.: US 10,178,881 B2
(45) Date of Patent: *Jan. 15, 2019

(54) ELECTRONIC CIGARETTE

(71) Applicant: FONTEM HOLDINGS 1 B.V., Amsterdam (NL)

(72) Inventor: Lik Hon, Beijing (CN)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/908,250

(22) Filed: Feb. 28, 2018

(65) Prior Publication Data

US 2018/0184721 A1 Jul. 5, 2018

Related U.S. Application Data

(63) Continuation of application No. 15/634,698, filed on Jun. 27, 2017, which is a continuation of application (Continued)

(30) Foreign Application Priority Data

May 16, 2006 (CN) ..................... 2006 2 0090805 U

(51) Int. Cl.
*A24F 47/00* (2006.01)
*H05B 1/02* (2006.01)
(Continued)

(52) U.S. Cl.
CPC .......... *A24F 47/008* (2013.01); *A24F 47/002* (2013.01); *A24F 47/004* (2013.01);
(Continued)

(58) Field of Classification Search
CPC ...... A24F 47/00–47/008; A61M 15/06; A61M 15/009; A61M 15/0091; A61M 2202/0468
See application file for complete search history.

(56) References Cited

U.S. PATENT DOCUMENTS 705,919 A 7/1902 Gill
1,147,416 A 7/1915 MacDonald
(Continued)

FOREIGN PATENT DOCUMENTS

CA 2752134 A1 11/2004
CA 2562581 A1 3/2005
(Continued)

OTHER PUBLICATIONS

Chen, Zhiyong—Request to Invalidate CN Utility Model Patent No. 200620090805.0 with English Translation, May 21, 2013.
(Continued)

*Primary Examiner* — Michael H. Wilson
*Assistant Examiner* — Yana B Krinker
(74) *Attorney, Agent, or Firm* — Perkins Coie LLP; Kenneth H. Ohriner

(57) ABSTRACT

An electronic cigarette includes a battery assembly, an atomizer assembly and a cigarette bottle assembly. An external thread electrode is located in one end of battery assembly. An internal thread electrode is located in one end of atomizer assembly. The battery assembly and the atomizer assembly are connected by the screwthread electrode. The cigarette bottle assembly is inserted into the other end of the atomizer assembly and both form a cigarette type or cigar type body.

16 Claims, 10 Drawing Sheets

Related U.S. Application Data

No. 15/158,421, filed on May 18, 2016, now Pat. No. 9,808,033, which is a continuation of application No. 13/754,521, filed on Jan. 30, 2013, now Pat. No. 9,370,205, which is a continuation of application No. 12/226,819, filed as application No. PCT/CN2007/001576 on May 15, 2007, now Pat. No. 8,375,957.

(51) Int. Cl.

| | | |
|---|---|---|
| H05B 3/06 | (2006.01) | |
| H05B 3/42 | (2006.01) | |
| F22B 1/28 | (2006.01) | |
| H01M 2/10 | (2006.01) | |
| H01M 10/42 | (2006.01) | |
| H01M 10/46 | (2006.01) | |
| H02J 7/00 | (2006.01) | |
| H01M 10/48 | (2006.01) | |
| H05B 3/03 | (2006.01) | |
| H01M 10/0525 | (2010.01) | |

(52) U.S. Cl.
CPC ........... *F22B 1/284* (2013.01); *H01M 2/1022* (2013.01); *H01M 2/1055* (2013.01); *H01M 10/0525* (2013.01); *H01M 10/425* (2013.01); *H01M 10/46* (2013.01); *H01M 10/488* (2013.01); *H02J 7/0042* (2013.01); *H02J 7/0052* (2013.01); *H05B 1/0244* (2013.01); *H05B 1/0291* (2013.01); *H05B 1/0297* (2013.01); *H05B 3/03* (2013.01); *H05B 3/06* (2013.01); *H05B 3/42* (2013.01); *H01M 2220/30* (2013.01)

(56) References Cited

U.S. PATENT DOCUMENTS

| | | | | |
|---|---|---|---|---|
| 2,057,353 | A | * | 10/1936 | Whittemore .......... A24F 47/008 128/203.27 |
| 2,461,664 | A | | 2/1949 | Smith |
| 3,200,819 | A | * | 8/1965 | Gilbert .................. A24F 47/008 128/202.21 |
| 3,234,357 | A | | 2/1966 | Seuthe |
| 3,281,637 | A | | 10/1966 | Hultquist |
| 3,431,393 | A | | 3/1969 | Katsuda |
| 3,479,561 | A | | 11/1969 | Janning |
| 3,685,522 | A | | 8/1972 | Kleinhans |
| 3,703,042 | A | | 11/1972 | Smith |
| 4,531,178 | A | | 7/1985 | Uke |
| 4,676,237 | A | | 6/1987 | Wood |
| 4,765,347 | A | | 8/1988 | Sensabaugh |
| 4,771,295 | A | | 9/1988 | Baker |
| 4,945,448 | A | | 7/1990 | Bremenour |
| 4,945,929 | A | | 8/1990 | Egilmex |
| 4,947,874 | A | | 8/1990 | Brooks |
| 4,968,263 | A | | 11/1990 | Silbernagel |
| 4,981,522 | A | | 1/1991 | Nichols |
| 4,990,939 | A | | 2/1991 | Sekiya |
| 5,060,671 | A | | 10/1991 | Counts |
| 5,144,962 | A | | 9/1992 | Counts |
| 5,177,424 | A | | 1/1993 | Connors |
| 5,266,746 | A | | 11/1993 | Nishihara |
| 5,372,148 | A | | 12/1994 | McCafferty |
| 5,666,977 | A | | 9/1997 | Higgins |
| 5,703,633 | A | | 12/1997 | Gehrer |
| 5,743,251 | A | | 4/1998 | Howell |
| 5,745,985 | A | | 5/1998 | Ghosh |
| 5,894,841 | A | * | 4/1999 | Voges ................... A24F 47/008 128/200.14 |
| 6,155,268 | A | | 12/2000 | Takeuchi |
| 6,196,218 | B1 | | 3/2001 | Voges |
| 6,234,167 | B1 | | 5/2001 | Cox |
| 6,311,561 | B1 | | 11/2001 | Bang |
| 6,322,268 | B1 | | 11/2001 | Kaufmann |
| 6,598,607 | B2 | | 7/2003 | Adiga |
| 6,601,776 | B1 | | 8/2003 | Oljaca |
| 6,715,494 | B1 | | 4/2004 | McCoy |
| 7,726,320 | B2 | | 6/2010 | Robinson |
| 8,156,944 | B2 | | 4/2012 | Hon |
| 2003/0033055 | A1 | | 2/2003 | McRae |
| 2003/0189826 | A1 | | 10/2003 | Yoon |
| 2004/0149282 | A1 | | 8/2004 | Hickle |
| 2004/0261802 | A1 | | 12/2004 | Griffin |
| 2005/0016550 | A1 | | 1/2005 | Katase |
| 2006/0196518 | A1 | | 9/2006 | Hon |
| 2007/0267031 | A1 | | 11/2007 | Hon |
| 2008/0257367 | A1 | | 10/2008 | Paterno |
| 2009/0126745 | A1 | | 5/2009 | Hon |

FOREIGN PATENT DOCUMENTS

| | | |
|---|---|---|
| CA | 2647212 A1 | 5/2006 |
| CN | 1135860 A | 11/1996 |
| CN | 1196660 A | 11/1996 |
| CN | 1191696 A | 9/1998 |
| CN | 2293957 Y | 10/1998 |
| CN | 1233436 A | 11/1999 |
| CN | 1252961 A | 5/2000 |
| CN | 1106812 C | 4/2003 |
| CN | 1530041 A | 9/2004 |
| CN | 1541577 A | 11/2004 |
| CN | 1575673 A | 2/2005 |
| CN | 2719043 Y | 8/2005 |
| CN | 2777995 Y | 5/2006 |
| CN | 201797997 U | 4/2011 |
| CN | 202026802 U | 11/2011 |
| CN | 202026804 U | 11/2011 |
| EP | 0057243 A1 | 8/1982 |
| EP | 0501419 A1 | 9/1992 |
| EP | 0845220 A1 | 12/1997 |
| EP | 0845220 B1 | 6/1998 |
| EP | 1736065 A1 | 8/2005 |
| EP | 1584910 A1 | 10/2005 |
| EP | 01618803 A | 1/2006 |
| EP | 01618808 A | 1/2006 |
| GB | 588117 A | 5/1947 |
| WO | 1994021317 A1 | 9/1994 |
| WO | 2000028843 A1 | 5/2000 |
| WO | 2004080216 A1 | 9/2004 |
| WO | 2005099494 A1 | 10/2005 |

OTHER PUBLICATIONS

Collins, John M., *Fontem v. NJOY, Inc.*, Case 14-cv-01645 GW (MRW) and consolidated cases, Expert Report—Invalidity (Excerpts), Jun. 18, 2015.

Collins, John M., Expert Report—Invalidity, CV14-01645, Jun. 18, 2015—Exhibit 103, certified English translation of CN2719043 Hon '043 Translation.

Collins, John M., Expert Report—Invalidity, CV14-01645, Jun. 18, 2015—Exhibit 104, certified English translation of WO2005099494 Hon '494 Translation.

Collins, John M., Expert Report—Invalidity, CV14-01645, Jun. 18, 2015—Exhibit 78, TECHPOWERUP, www.techpowerup.com— "What is a MOSFET, what does it look like, and how does it work?"—published May 24, 2004.

Collins, John M., Expert Report—Invalidity, CV14-01645— Appendix F-1 Invalidity Claim Chart for U.S. Pat. No. 8,375,957, Jun. 18, 2015.

Collins, John M., Expert Report—Invalidity, CV14-01645— Appendix F-2 Invalidity Claim Chart for U.S. Pat. No. 8,375,957, Jun. 18, 2015.

Collins, John M., Expert Report—Invalidity, CV14-01645— Appendix F-3 Invalidity Claim Chart for U.S. Pat. No. 8,375,957, Jun. 18, 2015.

Collins, John M., Expert Report—Invalidity, CV14-01645— Appendix F-4 Invalidity Claim Chart for U.S. Pat. No. 8,375,957, Jun. 18, 2015.

Collins, John M., Expert Report—Invalidity, CV14-01645— Appendix J-1 Invalidity Claim Chart for U.S. Pat. No. 8,863,752, Jun. 18, 2015.

(56) References Cited

OTHER PUBLICATIONS

Collins, John M., Expert Report—Invalidity, CV14-01645—Appendix J-2 Invalidity Claim Chart for U.S. Pat. No. 8,863,752, Jun. 18, 2015.
Collins, John M., Expert Report—Invalidity, CV14-01645—Appendix J-3 Invalidity Claim Chart for U.S. Pat. No. 8,863,752, Jun. 18, 2015.
Collins, John M., Expert Report—Invalidity, CV14-01645—Appendix J-4 Invalidity Claim Chart for U.S. Pat. No. 8,863,752, Jun. 18, 2015.
Collins, John M., Expert Report—Invalidity, CV14-01645—Appendix J-5 Invalidity Claim Chart for U.S. Pat. No. 8,863,752, Jun. 18, 2015.
Collins, John M., Expert Report—Invalidity, CV14-01645—Appendix J-6 Invalidity Claim Chart for U.S. Pat. No. 8,863,752, Jun. 18, 2015.
Hewlett-Packard, Thermal Ink-Jet Print Cartridge Designers Guide, Apr. 20, 1999.
Indian Patent Office, First Examination Report for IN8529/DELNP/2008, Jun. 25, 2015.
Indian Patent Office, Decision of Refusal for IN8529/DELNP/2008, dated Nov. 24, 2017.
IP Australia, Patent Examination Report No. 1 for AU2007250368, dated Aug. 9, 2012.
IP Office New Zealand, Exam Report for NZ572310, dated Apr. 29, 2010.
ITC Limited, Opposition to Grant of Patent against IN8529/DELNP/2008, May 11, 2015.
ITC Limited, Opposition to Grant of Patent against IN8529/DELNP/2008, May 11, 2015, D1 Equivalent—EP1736065.
ITC Limited, Opposition to Grant of Patent against IN8529/DELNP/2008, May 11, 2015, D1—CN2719043.
ITC Limited, Opposition to Grant of Patent against IN8529/DELNP/2008, May 11, 2015, D2—WO1994021317.
ITC Limited, Opposition to Grant of Patent against IN8529/DELNP/2008, May 11, 2015, D3—U.S. Pat. No. 6,601,776.
ITC Limited, Opposition to Grant of Patent against IN8529/DELNP/2008, May 11, 2015, D4—EP01618803A.
ITC Limited, Opposition to Indian Patent Application No. 8529/DELNP/2008—Reply to Claim Amendments, Nov. 24, 2016.
JT International S.A., Petition for Inter Partes Review of U.S. Pat. No. 8,375,957—IPR2015-01513, Paper 1, Jun. 26, 2015.
JT International S.A., IPR2015-01513, Exhibit 1001, U.S. Pat. No. 8,375,957 to Hon, Jun. 26, 2015.
JT International S.A., IPR2015-01513, Exhibit 1002, Schuster Expert Declaration, Jun. 26, 2015.
JT International S.A., IPR2015-01513, Exhibit 1003, Canadian Patent Application No. 2 752 134 to Hon, Jun. 26, 2015.
JT International S.A., IPR2015-01513, Exhibit 1004, U.S. Pat. No. 6,234,167 to Cox, Jun. 26, 2015.
JT International S.A., IPR2015-01513, Exhibit 1005, EP 0 845 220 A1 to Susa, Jun. 26, 2015.
JT International S.A., IPR2015-01513, Exhibit 1006, U.S. Pat. No. 5,060,671 to Counts, Jun. 26, 2015.
JT International S.A., IPR2015-01513, Exhibit 1007, U.S. Pat. No. 6,155,268 to Takeuchi, Jun. 26, 2015.
JT International S.A., IPR2015-01513, Exhibit 1008, WO 00/28843 A1 to Pienemann, Jun. 26, 2015.
JT International S.A., IPR2015-01513, Exhibit 1009, Certified English translation of WO 00/28843 A1 to Pienemann, Jun. 26, 2015.
JT International S.A., IPR2015-01513, Exhibit 1010, CN 2719043 to Hon, Jun. 26, 2015.
JT International S.A., IPR2015-01513, Exhibit 1011, Certified English translation of CN 2719043 to Hon, Jun. 26, 2015.
JT International S.A., IPR2015-01513, Exhibit 1012, U.S. Pat. No. 2,057,353 to Whittemore, Jun. 26, 2015.
JT International S.A., IPR2015-01513, Exhibit 1013, U.S. Patent Publication No. 2003/0033055 A1 to McRae, Jun. 26, 2015.
JT International S.A., IPR2015-01513, Exhibit 1014, CN200620090805 to Hon, Jun. 26, 2015.
JT International S.A., IPR2015-01513, Exhibit 1015, Certified English translation of CN200620090805 to Hon, Jun. 26, 2015.
JT International S.A., IPR2015-01513, Exhibit 1016, Oct. 5, 2010 Office Action ('957), dated Jun. 26, 2015.
JT International S.A., IPR2015-01513, Exhibit 1017, Mar. 7, 2011 Response (957), Jun. 26, 2015.
JT International S.A., IPR2015-01513, Exhibit 1018, Jun. 8, 2011 Office Action ('957), dated Jun. 26, 2015.
JT International S.A., IPR2015-01513, Exhibit 1019, Dec. 8, 2011 Response ('957), Jun. 26, 2015.
JT International S.A., IPR2015-01513, Exhibit 1020, Jan. 9, 2012 Office Action ('957), dated Jun. 26, 2015.
JT International S.A., IPR2015-01513, Exhibit 1021, May 9, 2012 Response ('957), Jun. 26, 2015.
JT International S.A., IPR2015-01513, Exhibit 1022, Aug. 7, 2012 Office Action ('957), dated Jun. 26, 2015.
JT International S.A., IPR2015-01513, Exhibit 1023, Aug. 29, 2012 Response ('957), Jun. 26, 2015.
JT International S.A., IPR2015-01513, Exhibit 1024, Dec. 17, 2012 Notice of Allowance ('957), dated Jun. 26, 2015.
JT International S.A., IPR2015-01513, Exhibit 1025, McGraw-Hill Dictionary of Scientific and Technical Terms (5th ed. 1994), Jun. 26, 2015.
JT International S.A., IPR2015-01513, Exhibit 1026, Academic Press Dictionary of Science and Technology (1992), Jun. 26, 2015.
JT International S.A., IPR2015-01513, Exhibit 1027, American Heritage Dictionary of the English Language (1996), Jun. 26, 2015.
JT International S.A., IPR2015-01513, Exhibit 1028, KR 10-0469625 to Kim, Jun. 26, 2015.
JT International S.A., IPR2015-01513, Exhibit 1029, Certified English translation of KR 10-0469625 to Kim, Jun. 26, 2015.
JT International S.A., IPR2015-01513, Exhibit 1030, U.S. Pat. No. 1,446,087 to Griffin, Jun. 26, 2015.
JT International S.A., IPR2015-01513, Exhibit 1031, Curriculum Vitae of Jeffrey Arthur Schuster, Ph.D., Jun. 26, 2015.
JT International S.A., IPR2015-01513, Exhibit 1032, J.A. Speck, Mechanical Fastening, Joining and Assembly (1997), Jun. 26, 2015.
JT International S.A., IPR2015-01513, Exhibit 1033, U.S. Pat. No. 705,919 to Gill, Jun. 26, 2015.
JT International S.A., IPR2015-01513, Exhibit 1034, U.S. Pat. No. 980,830 to Patterson, Jun. 26, 2015.
JT International S.A., IPR2015-01513, Exhibit 1035, U.S. Pat. No. 6,070,992 to Schnell, Jun. 26, 2015.
JT International S.A., IPR2015-01513, Exhibit 1036, U.S. Pat. No. 3,934,117 to Schladitz, Jun. 26, 2015.
JT International S.A., IPR2015-01513, Exhibit 1037, U.S. Pat. No. 4,531,178 to Uke, Jun. 26, 2015.
JT International S.A., IPR2015-01513, Exhibit 1038, U.S. Pat. No. 5,177,424 to Connors, Jun. 26, 2015.
JT International S.A., IPR2015-01513, Exhibit 1039, U.S. Pat. No. 6,232,784 to Dulasky, Jun. 26, 2015.
JT International S.A., Petition for Inter Partes Review of U.S. Pat. No. 8,863,752—IPR2015-01604, Paper 1, Jul. 20, 2015.
JT International S.A., IPR2015-01604, Exhibit 1001, U.S. Pat. No. 8,863,752 to Hon, Jul. 20, 2015.
JT International S.A., IPR2015-01604, Exhibit 1002, Declaration of Jeffrey A. Schuster, Ph.D., Jul. 20, 2015.
JT International S.A., IPR2015-01604, Exhibit 1003, U.S. Pat. No. 8,375,957 Certificate of Correction, Jul. 20, 2015.
JT International S.A., IPR2015-01604, Exhibit 1004, '752 Patent Application as Filed, Jul. 20, 2015.
JT International S.A., IPR2015-01604, Exhibit 1005, Restriction Requirement, dated Jul. 20, 2015.
JT International S.A., IPR2015-01604, Exhibit 1006, Response to Restriction Requirement, dated Jul. 20, 2015.
JT International S.A., IPR2015-01604, Exhibit 1007, Non-Final Office Action, dated Jul. 20, 2015.
JT International S.A., IPR2015-01604, Exhibit 1008, Response to Non-Final Office Action, dated Jul. 20, 2015.
JT International S.A., IPR2015-01604, Exhibit 1009, Notice of Allowance, dated Jul. 20, 2015.

(56) References Cited

OTHER PUBLICATIONS

JT International S.A., IPR2015-01604, Exhibit 1010, McGraw-Hill Dictionary of Scientific and Technical Terms ("assembly") ("component") ("electrode") ("pore") ("porous") ("screwthread"), Jul. 20, 2015.
JT International S.A., IPR2015-01604, Exhibit 1011, American Heritage Dictionary ("atomize ") ("flow"), Jul. 20, 2015.
JT International S.A., IPR2015-01604 Exhibit 1012, Merriam-Webster.com ("aerosol") ("atomizer") ("contain") ("housing") ("insert") ("paper") ("permeable") ("store"), Jul. 20, 2015.
JT International S.A., IPR2015-01604, Exhibit 1013, Academic Press Dictionary of Science and Technology ("permeability") ("solid"), Jul. 20, 2015.
JT International S.A., IPR2015-01604, Exhibit 1014, Canadian Patent Application No. 2 752 134 to Hon, Jul. 20, 2015.
JT International S.A., IPR2015-01604, Exhibit 1015, U.S. Pat. No. 6,155,268 to Takeuchi, Jul. 20, 2015.
JT International S.A., IPR2015-01604, Exhibit 1016, WO 00/28843 A1 to Pienemann, Jul. 20, 2015.
JT International S.A., IPR2015-01604, Exhibit 1017, Certified English translation of WO 00/28843 A1 to Pienemann, Jul. 20, 2015.
JT International S.A., IPR2015-01604, Exhibit 1018, EP 0 845 220 A1 to Susa, Jul. 20, 2015.
JT International S.A., IPR2015-01604, Exhibit 1019, J.A. Speck, Mechanical Fastening,Joining and Assembly (1997), Jul. 20, 2015.
Logic Technology Products, Inc., Petition for Inter Partes Review of U.S. Pat. No. 8,375,957—IPR2015-00098, Oct. 21, 2014.
Logic Technology Products, Inc., IPR2015-00098, Exhibit 1001—U.S. Pat. No. 8,375,957, Oct. 21, 2014.
Logic Technology Products, Inc., IPR2015-00098, Exhibit 1002, Declaration of Gregory Buckner, Ph.D., Oct. 21, 2014.
Logic Technology Products, Inc., IPR2015-00098, Exhibit 1003, China Patent CN 2719043—issue date Aug. 24, 2005, Oct. 21, 2014.
Logic Technology Products, Inc., IPR2015-00098, Exhibit 1004, Certified English translation of CN 2719043 pursuant to 37 C.F.R. 42.63(b), Oct. 21, 2014.
Logic Technology Products, Inc., IPR2015-00098, Exhibit 1005, U.S. publication 2007/0267031 ("Hon '031"), which is the U.S. equivalent of CN 2719043, Oct. 21, 2014.
Logic Technology Products, Inc., IPR2015-00098, Exhibit 1006, CA 2562581, which is the Canadian equivalent of CN 2719043, Oct. 21, 2014.
Logic Technology Products, Inc., IPR2015-00098, Exhibit 1007, U.S. Pat. No. 3,200,819 ("Gilbert")—issue date Aug. 17, 1965, Oct. 21, 2014.
Logic Technology Products, Inc., IPR2015-00098, Exhibit 1008, U.S. Pat. No. 2,057,353 ("Whittemore")—issue date Oct. 13, 1936, Oct. 21, 2014.
Logic Technology Products, Inc., IPR2015-00098, Exhibit 1009, U.S. Pat. No. 5,894,841 ("Voges")—issue date Apr. 20, 1999, Oct. 21, 2014.
Logic Technology Products, Inc., IPR2015-00098, Exhibit 1010, U.S. Pat. App. Pub. 2008/0257367 ("Paterno")—filed Apr. 23, 2007, Oct. 21, 2014.
Logic Technology Products, Inc., IPR2015-00098, Exhibit 1011, EP 0533599A1 ("Connors")—publication date Mar. 24, 1993, Oct. 21, 2014.
Logic Technology Products, Inc., IPR2015-00098, Exhibit 1012, Non-patent publication "What is a MOSFET, what does it look like, and how does it work?" dated May 24, 2004, printed from the Internet Archive, i.e., the Wayback machine, which was archived on Mar. 5, 2010 ("TechPowerUp"), Oct. 21, 2014.
Logic Technology Products, Inc., IPR2015-00098, Exhibit 1013, Non-patent publication "What is a MOSFET, what does it look like, and how does it work?" dated May 24, 2004, printed from the Internet Archive, i.e., the Wayback machine, which was archived on Jul. 20, 2011 ("TechPowerUp"), Oct. 21, 2014.
Logic Technology Products, Inc., IPR2015-00098, Exhibit 1014, PCT application No. PCT/CN2007/ 001576, filed on May 15, 2007, and Jan. 15, 2009 Chinese Declaration re CN Patent Application No. 200620090805 ("Hon '805"), Oct. 21, 2014.
Logic Technology Products, Inc., IPR2015-00098, Exhibit 1015, '957 patent file history, Oct. 29, 2008 Preliminary Amendment, dated Oct. 21, 2014.
Logic Technology Products, Inc., IPR2015-00098, Exhibit 1016, '957 patent file history, Oct. 5, 2010, Office Action, dated Oct. 21, 2014.
Logic Technology Products, Inc., IPR2015-00098, Exhibit 1017, '957 patent file history, Mar. 7, 2011, Response to Office Action, dated Oct. 21, 2014.
Logic Technology Products, Inc., IPR2015-00098, Exhibit 1018, '957 patent file history, Mar. 29, 2011, Applicant's "Marked-Up Specification", Oct. 21, 2014.
Logic Technology Products, Inc., IPR2015-00098, Exhibit 1019, '957 patent file history, Jun. 8, 2011, Office Action, dated Oct. 21, 2014.
Logic Technology Products, Inc., IPR2015-00098, Exhibit 1020, '957 patent file history, Dec. 8, 2011, Request for Continued Examination, dated Oct. 21, 2014.
Logic Technology Products, Inc., IPR2015-00098, Exhibit 1021, '957 patent file history, Jan. 9, 2012, Office Action, dated Oct. 21, 2014.
Logic Technology Products, Inc., IPR2015-00098, Exhibit 1022, '957 patent file history, May 9, 2012, Amendment, dated Oct. 21, 2014.
Logic Technology Products, Inc., IPR2015-00098, Exhibit 1023, '957 patent file history, Aug. 7, 2012, Office Action, dated Oct. 21, 2014.
Logic Technology Products, Inc., IPR2015-00098, Exhibit 1024, '957 patent file history, Aug. 29, 2012, Amendment, dated Oct. 21, 2014.
Logic Technology Products, Inc., IPR2015-00098, Exhibit 1025, '957 patent file history, Dec. 17, 2012, Notice of Allowance., dated Oct. 21, 2014.
Logic Technology Products, Inc., IPR2015-00098, Exhibit 1026, '957 patent file history, Jul. 2, 2013, Certificate of Correction, Oct. 21, 2014.
Logic Technology Products, Inc., IPR2015-00098, Exhibit 1027, U.S. Pat. No. 8,156,944 (Hon; Aerosol Electronic Cigarette), Oct. 21, 2014.
Logic Technology Products, Inc., IPR2015-00098, Exhibit 1028, Decision—Institution of Inter Partes Review in IPR2013-00387, Paper 7, Oct. 21, 2014.
Logic Technology Products, Inc., IPR2015-00098, Exhibit 1029, Curriculum Vitae of Gregory Buckner, Ph.D., Oct. 21, 2014.
Micro Pneumatic Logic, Inc., MPL Pressure Switch Solutions, (Product Brochure) (Mar. 11, 2006), http://www.pressureswitch.com/PDFs/2000_MPLBrochure.pdf [https://web.archive.org/web/20060311132419/http://www.pressureswitch.com/PDFs/2000_MPLBrochure.pdf], Mar. 11, 2006.
NJOY, Inc. et al., *Fontem* v. *NJOY, Inc.*, Case 14-cv-01645 GW (MRW) and consolidated cases, Defendants' Joint Invalidity Contentions, Aug. 7, 2014.
NJOY, Inc. et al., CV-14-01645 and consolidated cases, Defendants' Joint Invalidity Contentions,., Attachment D—Claim Charts for U.S. Pat. No. 8,375,957, Aug. 7, 2014.
NJOY, Inc. et al., *Fontem* v. *NJOY, Inc.*, Case 14-cv-01645 GW (MRW) and consolidated cases, Defendants' Joint Invalidity Contentions, Feb. 26, 2015.
NJOY, Inc. et al., CV-14-01645 and consolidated cases, Defendant's Joint Invalidity Contentions, Exhibit D—Claim Charts for U.S. Pat. No. 8,863,752, Feb. 26, 2015.
NJOY, Inc.'s Memorandum of Points and Authorities in Support of Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc.'s Declaration of Brent K. Yamashita in Support of Defendants' Motion for Leave to Amend Invalidity Contentions dated Jun. 29, 2015 and filed in *Fontem Ventures B.V.* v. *NJOY, Inc.*,

(56) References Cited

OTHER PUBLICATIONS

U.S. District Court, Central District of California, Consolidated Case No. CV 14-01645 GW (MRW) and related consolidated cases.
NJOY, Inc.'s Exhibit 1 to Defendants' Motion for Leave to Amend Invalidity Contentions dated Jun. 29, 2015 and filed in *Fontem Ventures B.V. v. NJOY, Inc.*, U.S. District Court, Central District of California, Consolidated Case No. CV 14-01645 GW (MRW) and related consolidated cases.
NJOY, Inc.'s Exhibit 2 to Defendants' Motion for Leave to Amend Invalidity Contentions dated Jun. 29, 2015 and filed in *Fontem Ventures B.V. v. NJOY, Inc.*, U.S. District Court, Central District of California, Consolidated Case No. CV 14-01645 GW (MRW) and related consolidated cases.
NJOY, Inc.'s Exhibit 3 to Defendants' Motion for Leave to Amend Invalidity Contentions dated Jun. 29, 2015 and filed in *Fontem Ventures B.V. v. NJOY, Inc.*, U.S. District Court, Central District of California, Consolidated Case No. CV 14-01645 GW (MRW) and related consolidated cases.
NJOY, Inc.'s Exhibit 4 to Defendants' Motion for Leave to Amend Invalidity Contentions dated Jun. 29, 2015 and filed in *Fontem Ventures B.V. v. NJOY, Inc.*, U.S. District Court, Central District of California, Consolidated Case No. CV 14-01645 GW (MRW) and related consolidated cases.
NJOY, Inc.'s Exhibit 5 to Defendants' Motion for Leave to Amend Invalidity Contentions dated Jun. 29, 2015 and filed in *Fontem Ventures B.V. v. NJOY, Inc.*, U.S. District Court, Central District of California, Consolidated Case No. CV 14-01645 GW (MRW) and related consolidated cases.
NJOY. Inc.'s production documents VLACHOS 0000061-72; *Fontem Ventures B.V. v. NJOY, Inc.*, U.S. District Court, Central District of California, Consolidated Case No. CV 1401645 Gw (Mrw) and related consolidated cases, Jun. 4, 2015.
NJOY. Inc.'s Reply Brief in Support of Defendants' Motion for Leave to Amend Invalidity Contentions dated Jul. 13, 2015 and filed in *Fontem Ventures B.V. v. Njoy, Inc.*, U.S. District Court, Central District of California, Consolidated Case No. CV 14-01645 GW (MRW) and related consolidated cases.
NJOY, Inc. et al, Petition for Inter Partes Review of U.S. Pat. No. 8,863,752—IPR2015-01301, May 29, 2015.
NJOY, Inc. et al, IPR2015-01301, Exhibit 1001, U.S. Pat. No. 8,863,752 ("the '752 patent"), May 29, 2015.
NJOY, Inc. et al, R2015-01301, Exhibit 1002, Declaration Samir Nayfeh, Ph.D. ("Nayfeh Decl."), May 29, 2015.
NJOY, Inc. et al, IPR2015-01301, Exhibit 1003, Canadian Pat. App. No. 2,752,134 ("Hon '134"), May 29, 2015.
NJOY, Inc. et al, IPR2015-01301, Exhibit 1004, U.S. Pat. No. 3,200,819 ("Gilbert"), May 29, 2015.
NJOY, Inc. et al, IPR2015-01301, Exhibit 1005, U.S. Pat. No. 6,155,268 ("Takeuchi"), May 29, 2015.
NJOY, Inc. et al, IPR2015-01301, Exhibit 1006, U.S. Pat. No. 1,446,087 ("Griffin"), May 29, 2015.
NJOY, Inc. et al, IPR2015-01301, Exhibit 1007, Markman Hearing/Claim Construction Order, *Fontem Ventures, B.V. v. NJOY, Inc.*, No. 14-cv-1645, Dkt. 133 (C.D. Cal. May 7, 2015), May 29, 2015.
NJOY, Inc. et al, IPR2015-01301, Exhibit 1008, Rulings on Claim Construction, *Fontem Ventures, B.V. v. Njoy, Inc.*, No. 14-cv-1645, Dkt. 65 (C.D. Cal. Jan. 29, 2015), May 29, 2015.
NJOY, Inc. et al, IPR2015-01301, Exhibit 1009, Joint Claim Construction and Prehearing Statement, *Fontem Ventures, B.V. v. Njoy, Inc.*, No. 14-cv-1645, Dkt. 93 (C.D. Cal. Mar. 19, 2015), May 29, 2015.
NJOY, Inc. et al, IPR2015-01301, Exhibit 1010, Revised Joint Claim Construction and Prehearing Statement, *Fontem Ventures, B.V. v. NJOY, Inc.*, No. 14-cv-1645, Dkt. 34 (C.D. Cal. Sep. 30, 2014), May 29, 2015.
NJOY, Inc. et al, IPR2015-01301, Exhibit 1011, Curriculum Vitae of Samir Nayfeh, Ph.D., May 29, 2015.
Nu Mark LLC, Answer to Complaint and Counterclaims in *Fontem Ventures B.V. v. Nu Mark LLC*, 16-CV-1259, Dkt. 034, Oct. 26, 2016.
Nu Mark LLC, Answer to Complaint and Counterclaims in *Fontem Ventures B.V. v. Nu Mark LLC*, 16-CV-2291, Dkt. 025, Jun. 27, 2016.
Nu Mark LLC, First Amended Answer and Counterclaims in *Fontem Ventures B.V. v. Nu Mark LLC*, 16-CV-2291, Dkt. 042, Jul. 28, 2017.
Nu Mark LLC, Petition for Inter Partes Review of U.S. Pat. No. 8,375,957—IPR2016-01307, Jun. 28, 2016.
Nu Mark LLC, IPR2016-01307, Ex. 1001, U.S. Pat. No. 8,375,957, Jun. 28, 2016.
Nu Mark LLC, IPR2016-01307, Ex. 1002, File History for U.S. Pat. No. 8,375,957 (excerpts), Jun. 28, 2016.
Nu Mark LLC, IPR2016-01307, Ex. 1003, Declaration of Dr. John Collins, Jun. 28, 2016.
Nu Mark LLC, IPR2016-01307, Ex. 1004, U.S. Pat. No. 6,155,268 ("Takeuchi"), Jun. 28, 2016.
Nu Mark LLC, IPR2016-01307, Ex. 1005, U.S. Pat. No. 2,057,353 ("Whittemore"), Jun. 28, 2016.
Nu Mark LLC, IPR2016-01307, Ex. 1006, U.S. Pat. No. 4,947,874 ("Brooks"), Jun. 28, 2016.
Nu Mark LLC, IPR2016-01307, Ex. 1007, European Patent Application No. EP0845220 B1 ("Susa"), Jun. 28, 2016.
Nu Mark LLC, IPR2016-01307, Ex. 1008, J.A. Speck, Mechanical Fastening, Joining, and Assembly (1997) (excerpt), Jun. 28, 2016.
Nu Mark LLC, IPR2016-01307, Ex. 1009, McGraw-Hill Dictionary of Scientific and Technical Terms, McGraw-Hill Companies, Inc., (6th ed. 2003) (excerpt), Jun. 28, 2016.
Nu Mark LLC, IPR2016-01307, Ex. 1010, Invalidation Decision (No. WX15007), Patent Reexamination Board of the State Intellectual Property Office of the People's Republic of China (Jun. 13, 2010), with certified translation., Jun. 28, 2016.
Nu Mark LLC, IPR2016-01307, Ex. 1011, U.S. Patent Application No. 2006/0093977 A1 ("Pellizzari I"), Jun. 28, 2016.
Nu Mark LLC, IPR2016-01307, Ex. 1012, U.S. Pat. No. 7,059,307 ("Pellizzari II"), Jun. 28, 2016.
Nu Mark LLC, IPR2016-01307, Ex. 1013 U.S. Pat. No. 3,200,819 ("Gilbert"), Jun. 28, 2016.
Nu Mark LLC, IPR2016-01307, Ex. 1014 U.S. Pat. No. 5,894,841 ("Voges"), Jun. 28, 2016.
Nu Mark LLC, IPR2016-01307, Ex. 1015 U.S. Pat. No. 5,743,251 ("Howell"), Jun. 28, 2016.
Nu Mark LLC, IPR2016-01307, Ex. 1016 U.S. Pat. No. 2,461,664 ("Smith"), Jun. 28, 2016.
Nu Mark LLC, IPR2016-01307, Ex. 1017 U.S. Pat. No. 3,234,357 ("Eberhard"), Jun. 28, 2016.
Nu Mark LLC, IPR2016-01307, Ex. 1018 U.S. Pat. No. 5,745,985 ("Ghosh"), Jun. 28, 2016.
Nu Mark LLC, IPR2016-01307, Ex. 1019 U.S. Pat. No. 4,676,237 ("Wood"), Jun. 28, 2016.
Nu Mark LLC, IPR2016-01307, Ex. 1020 U.S. Pat. No. 438,310 ("Edison"), Jun. 28, 2016.
Nu Mark LLC, IPR2016-01307, Ex. 1021 U.S. Pat. No. 4,945,448 ("Bremenour"), Jun. 28, 2016.
Nu Mark LLC, IPR2016-01307, Ex. 1022 R. Messier, Joining of Materials and Structures (2004) (excerpt), Jun. 28, 2016.
Nu Mark LLC, IPR2016-01307, Ex. 1023 U.S. Pat. No. 2,442,004 ("Hayward-Butt"), Jun. 28, 2016.
Nu Mark LLC, IPR2016-01307, Ex. 1024 U.S. Pat. No. 5,177,424 ("Connors"), Jun. 28, 2016.
Nu Mark LLC, IPR2016-01307, Ex. 1025 *Fontem Ventures B.V. et al. v. Nu Mark LLC*, 2:16-cv-02291 (C.D. Cal. Apr. 4, 2016), D.I. 1 (excerpt) ("Complaint"), Jun. 28, 2016.
Nu Mark LLC, IPR2016-01307, Ex. 1026 U.S. Pat. No. 6,501,052 ("Cox"), Jun. 28, 2016.
Nu Mark LLC, IPR2016-01307, Ex. 1027 U.S. Pat. No. 6,491,233 ("Nichols"), Jun. 28, 2016.
Nu Mark LLC, IPR2016-01307, Ex. 1028 U.S. Pat. No. 1,084,304 ("Vaughn"), Jun. 28, 2016.
Nu Mark LLC, IPR2016-01307, Ex. 1029 U.S. Pat. No. 5,266,746 ("Nishihara"), Jun. 28, 2016.
Nu Mark LLC, IPR2016-01307, Ex. 1030 U.S. Pat. No. 4,968,263 ("Silbernagel"), Jun. 28, 2016.

(56) References Cited

OTHER PUBLICATIONS

Nu Mark LLC, Petition for Inter Partes Review of U.S. Pat. No. 8,863,752—IPR2016-01309, Jun. 28, 2016.
Nu Mark LLC, IPR2016-01309, Ex. 1001 U.S. Pat. No. 8,863,752, Jun. 28, 2016.
Nu Mark LLC, IPR2016-01309, Ex. 1002 File History for U.S. Pat. No. 8,863,752, Jun. 28, 2016.
Nu Mark LLC, IPR2016-01309, Ex. 1003 Declaration of Dr. John Collins, Jun. 28, 2016.
Nu Mark LLC, IPR2016-01309, Ex. 1004 U.S. Pat. No. 6,155,268 ("Takeuchi"), Jun. 28, 2016.
Nu Mark LLC, IPR2016-01309, Ex. 1005 U.S. Pat. No. 2,057,353 ("Whittemore"), Jun. 28, 2016.
Nu Mark LLC, IPR2016-01309, Ex. 1006 U.S. Pat. No. 4,947,874 ("Brooks"), Jun. 28, 2016.
Nu Mark LLC, IPR2016-01309, Ex. 1007 European Patent Application No. EP0845220 B1 ("Susa"), Jun. 28, 2016.
Nu Mark LLC, IPR2016-01309, Ex. 1008 J.A. Speck, Mechanical Fastening, Joining, and Assembly (1997) (excerpt), Jun. 28, 2016.
Nu Mark LLC, IPR2016-01309, Ex. 1009 McGraw-Hill Dictionary of Scientific and Technical Terms, McGraw-Hill Companies, Inc., (6th ed. 2003) (excerpt), Jun. 28, 2016.
Nu Mark LLC, IPR2016-01309, Ex. 1010 Invalidation Decision (No. WX15007), Patent Reexamination Board of the State Intellectual Property Office of the People's Republic of China (Jun. 13, 2010), with certified translation.
Nu Mark LLC, IPR2016-01309, Ex. 1011 U.S. Patent Application No. 2006/0093977 A1 ("Pellizzari I"), Jun. 28, 2016.
Nu Mark LLC, IPR2016-01309, Ex. 1012 U.S. Pat. No. 7,059,307 ("Pellizzari II"), Jun. 28, 2016.
Nu Mark LLC, IPR2016-01309, Ex. 1013 U.S. Pat. No. 3,200,819 (" Gilbert"), Jun. 28, 2016.
Nu Mark LLC, IPR2016-01309, Ex. 1014 U.S. Pat. No. 5,894,841 ("Voges"), Jun. 28, 2016.
Nu Mark LLC, IPR2016-01309, Ex. 1015 U.S. Pat. No. 5,743,251 ("Howell"), Jun. 28, 2016.
Nu Mark LLC, IPR2016-01309, Ex. 1016 U.S. Pat. No. 2,461,664 ("Smith"), Jun. 28, 2016.
Nu Mark LLC, IPR2016-01309, Ex. 1017 U.S. Pat. No. 3,234,357 ("Eberhard"), Jun. 28, 2016.
Nu Mark LLC, IPR2016-01309, Ex. 1018 U.S. Pat. No. 5,745,985 ("Ghosh"), Jun. 28, 2016.
Nu Mark LLC, IPR2016-01309, Ex. 1019 U.S. Pat. No. 4,676,237 ("Wood"), Jun. 28, 2016.
Nu Mark LLC, IPR2016-01309, Ex. 1020 U.S. Pat. No. 438,310 ("Edison"), Jun. 28, 2016.
Nu Mark LLC, IPR2016-01309, Ex. 1021 U.S. Pat. No. 4,945,448 ("Bremenour"), Jun. 28, 2016.
Nu Mark LLC, IPR2016-01309, Ex. 1022 R. Mesler, Joining of Materials and Structures (2004), Jun. 28, 2016.
Nu Mark LLC, IPR2016-01309, Ex. 1023 U.S. Pat. No. 2,442,004 ("Hayward-Butt"), Jun. 28, 2016.
Nu Mark LLC, IPR2016-01309, Ex. 1024 U.S. Pat. No. 6,501,052 ("Cox"), Jun. 28, 2016.
Nu Mark LLC, IPR2016-01309, Ex. 1025 U.S. Pat. No. 6,491,233 ("Nichols"), Jun. 28, 2016.
Nu Mark LLC, IPR2016-01309, Ex. 1026 U.S. Pat. No. 1,084,304 ("Vaughn"), Jun. 28, 2016.
Nu Mark LLC, Petition for Inter Partes Review of U.S. Pat. No. 9,326,550—IPR2016-01707, Paper 1 Petition, Aug. 31, 2016.
Nu Mark LLC, IPR2016-01707, Ex. 1001 U.S. Pat. No. 9,326,550 (the "550 Patent"), Aug. 31, 2016.
Nu Mark LLC, IPR2016-01707, Ex. 1002 File History for U.S. Appl. No. 13/754,521 (the "521 Application") (issued as U.S. Pat. No. 9,370,205) (excerpt), Aug. 31, 2016.
Nu Mark LLC, IPR2016-01707, Ex. 1003 Declaration of John M. Collins, Ph.D., Aug. 31, 2016.
Nu Mark LLC, IPR2016-01707, Ex. 1004 Curriculum Vitae of Dr. John M. Collins, Aug. 31, 2016.
Nu Mark LLC, IPR2016-01707, Ex. 1005 U.S. Pat. App. Pub. No. 2009/0126745 ("Hon 745"), Aug. 31, 2016.
Nu Mark LLC, IPR2016-01707, Ex. 1006 File History for U.S. Appl. No. 12/226,819 ("The 819 Application") (issued as U.S. Pat. No. 8,375,957) (excerpt), Aug. 31, 2016.
Nu Mark LLC, IPR2016-01707, Ex. 1007 U.S. Pat. No. 8,375,957 ("The 957 Patent"), Aug. 31, 2016.
Nu Mark LLC, IPR2016-01707, Ex. 1008 Decision Instituting IPR2014-01300 (Paper 8), Aug. 31, 2016.
Nu Mark LLC, IPR2016-01707, Ex. 1009 Certified Translation of CN 200620090805 (Chinese original included), Aug. 31, 2016.
Nu Mark LLC, IPR2016-01707, Ex. 1010 Claim Construction Order, *Fontem Ventures B.V. et al.* v. *NJOY, Inc. et al.*, Civil Action No. 2:14-cv-1645 (C.D. Cal.), Jan. 29, 2015 [DI-65], Aug. 31, 2016.
Nu Mark LLC, IPR2016-01707, Ex. 1011 Complaint, *Fontem Ventures B.V., et al.* v. *Nu Mark LLC*, Case No. 2:16-cv-04537 (excerpt), Aug. 31, 2016.
Nu Mark LLC, IPR2016-01707, Ex. 1012 U.S. Pat. No. 8,689,805 (the "805 Patent"), Aug. 31, 2016.
Nu Mark LLC, IPR2016-01707, Ex. 1013 File History for U.S. Appl. No. 13/426,817 (issued as U.S. Pat. No. 8,689,805) (excerpt), Aug. 31, 2016.
Nu Mark LLC, IPR2016-01707, Ex. 1014 Certified Translation of WO 2007/131450 (Chinese original included), Aug. 31, 2016.
Nu Mark LLC, IPR2016-01707, Ex. 1015 Patent Owner Prelim. Resp., *Logic Technology Development, LLC* v. *Fontem Holdings 1 B.V.*, IPR2015-00098, Paper 7 (Feb. 18, 2015), Aug. 31, 2016.
Nu Mark LLC, IPR2016-01707, Ex. 1016 U.S. Pat. App. Pub. No. 2009/0188490, Aug. 31, 2016.
Nu Mark LLC, IPR2016-01707, Ex. 1017 File History for U.S. Appl. No. 14/720,288 ("The 288 Application") (issued as U.S. Pat. No. 9,326,550), Aug. 31, 2016.
Nu Mark LLC, Petition for Inter Partes Review of U.S. Pat. No. 9,326,550—IPR2017-00205, Paper 1 Petition, Nov. 4, 2016.
Nu Mark LLC, IPR2017-00205, Ex. 1001 U.S. Pat. No. 9,326,550, Nov. 4, 2016.
Nu Mark LLC, IPR2017-00205, Ex. 1002 File History for U.S. Pat. No. 9,326,550 (excerpts), Nov. 4, 2016.
Nu Mark LLC, IPR2017-00205, Ex. 1003 Declaration of Dr. John Collins, Nov. 4, 2016.
Nu Mark LLC, IPR2017-00205, Ex. 1004 U.S. Pat. No. 6,155,268 ("Takeuchi"), Nov. 4, 2016.
Nu Mark LLC, IPR2017-00205, Ex. 1005 U.S. Pat. No. 2,057,353 ("Whittemore"), Nov. 4, 2016.
Nu Mark LLC, IPR2017-00205, Ex. 1006 U.S. Pat. No. 4,947,874 ("Brooks"), Nov. 4, 2016.
Nu Mark LLC, IPR2017-00205, Ex. 1007 European Patent Application No. EP0845220 A1 ("Susa"), Nov. 4, 2016.
Nu Mark LLC, IPR2017-00205, Ex. 1008 J.A. Speck, Mechanical Fastening, Joining, and Assembly (1997) (excerpt), Nov. 4, 2016.
Nu Mark LLC, IPR2017-00205, Ex. 1009 McGraw-Hill Dictionary of Scientific and Technical Terms, McGraw-Hill Companies, Inc., (6th ed. 2003) (excerpt), Nov. 4, 2016.
Nu Mark LLC, IPR2017-00205, Ex. 1010 Invalidation Decision (No. WX15007), Patent Reexamination Board of the State Intellectual Property Office of the People's Republic of China (Jun. 13, 2010), with certified translation, Nov. 4, 2016.
Nu Mark LLC, IPR2017-00205, Ex. 1011 U.S. Patent Application No. 2006/0093977 A1 ("Pellizzari I"), Nov. 4, 2016.
Nu Mark LLC, IPR2017-00205, Ex. 1012 U.S. Pat. No. 7,059,307 ("Pellizzari II"), Nov. 4, 2016.
Nu Mark LLC, IPR2017-00205, Ex. 1013 U.S. Pat. No. 3,200,819 ("Gilbert"), Nov. 4, 2016.
Nu Mark LLC, IPR2017-00205, Ex. 1014 U.S. Pat. No. 5,894,841 ("Voges"), Nov. 4, 2016.
Nu Mark LLC, IPR2017-00205, Ex. 1015 U.S. Pat. No. 5,743,251 ("Howell"), Nov. 4, 2016.
Nu Mark LLC, IPR2017-00205, Ex. 1016 U.S. Pat. No. 2,461,664 ("Smith"), Nov. 4, 2016.
Nu Mark LLC, IPR2017-00205, Ex. 1017 U.S. Pat. No. 3,234,357 ("Eberhard"), Nov. 4, 2016.
Nu Mark LLC, IPR2017-00205, Ex. 1018 U.S. Pat. No. 5,745,985 ("Ghosh"), Nov. 4, 2016.

(56) References Cited

OTHER PUBLICATIONS

Nu Mark LLC, IPR2017-00205, Ex. 1019 U.S. Pat. No. 4,676,237 ("Wood"), Nov. 4, 2016.
Nu Mark LLC, IPR2017-00205, Ex. 1020 U.S. Pat. No. 438,310 ("Edison"), Nov. 4, 2016.
Nu Mark LLC, IPR2017-00205, Ex. 1021 U.S. Pat. No. 4,945,448 ("Bremenour"), Nov. 4, 2016.
Nu Mark LLC, IPR2017-00205, Ex. 1022 R. Messler, Joining of Materials and Structures (2004) (excerpt), Nov. 4, 2016.
Nu Mark LLC, IPR2017-00205, Ex. 1023 U.S. Pat. No. 2,442,004 ("Hayward-Butt"), Nov. 4, 2016.
Nu Mark LLC, IPR2017-00205, Ex. 1024 U.S. Pat. No. 5,177,424 ("Connors"), Nov. 4, 2016.
Nu Mark LLC, IPR2017-00205, Ex. 1025 U.S. Pat. No. 6,501,052 ("Cox"), Nov. 4, 2016.
Nu Mark LLC, IPR2017-00205, Ex. 1026 U.S. Pat. No. 6,491,233 ("Nichols"), Nov. 4, 2016.
Nu Mark LLC, IPR2017-00205, Ex. 1027 U.S. Pat. No. 1,084,304 ("Vaughn"), Nov. 4, 2016.
Nu Mark LLC, IPR2017-00205, Ex. 1028 U.S. Pat. No. 5,266,746 ("Nishihara"), Nov. 4, 2016.
Nu Mark LLC, IPR2017-00205, Ex. 1029 U.S. Pat. No. 4,968,263 ("Silbernagel"), Nov. 4, 2016.
Nu Mark LLC, IPR2017-00205, Ex. 1030 U.S. Patent Application No. 2009/0126745 A1 ("Hon"), Nov. 4, 2016.
Nu Mark LLC, IPR2017-00205, Ex. 1031 European Patent Application No. EP1584910 B1 ("Hayato"), Nov. 4, 2016.
Nu Mark LLC, IPR2017-00205, Ex. 1032 U.S. Pat. No. 6,311,561 ("Bang"), Nov. 4, 2016.
Nu Mark LLC, IPR2017-00205, Ex. 1033 European Patent Publication No. EP 2022349 A1, Nov. 4, 2016.
Nu Mark LLC, IPR2017-00205, Ex. 1034 *Nicocigs Limited* v. *Fontem Holdings 1 BV et al.*, British High Court of Justice, Approved Judgment (Sep. 2, 2016), Nov. 4, 2016.
Nu Mark LLC, IPR2017-00205, Ex. 1035 U.S. Patent Application No. 2004/0234916 A1 (Hale), Nov. 4, 2016.
Nu Mark LLC, IPR2017-00205, Ex. 1036 U.S. Pat. No. 4,922,901 ("Brooks 901"), Nov. 4, 2016.
Nu Mark LLC, Petition for Inter Partes Review of U.S. Pat. No. 9,326,551—IPR2016- 01706, Paper 1 Petition, Aug. 31, 2016.
Nu Mark LLC, IPR2016-01706, Ex. 1001 U.S. Pat. No. 9,326,551 (the "551 Patent"), Aug. 31, 2016.
Nu Mark LLC, IPR2016-01706, Ex. 1002 File History for U.S. Appl. No. 13/754,521 (the "521 Application") (issued as U.S. Pat. No. 9,370,205) (excerpt), Aug. 31, 2016.
Nu Mark LLC, IPR2016-01706, Ex. 1003 Declaration of John M. Collins, Ph.D., Aug. 31, 2016.
Nu Mark LLC, IPR2016-01706, Ex. 1004 Curriculum Vitae of Dr. John M. Collins, Aug. 31, 2016.
Nu Mark LLC, IPR2016-01706, Ex. 1005 U.S. Pat. App. Pub. No. 2009/0126745 ("Hon 745"), Aug. 31, 2016.
Nu Mark LLC, IPR2016-01706, Ex. 1006 File History for U.S. Appl. No. 12/226,819 ("the 819 Application") (issued as U.S. Pat. No. 8,375,957) (excerpt), Aug. 31, 2016.
Nu Mark LLC, IPR2016-01706, Ex. 1007 U.S. Pat. No. 8,375,957 ("the 957 Patent"), Aug. 31, 2016.
Nu Mark LLC, IPR2016-01706, Ex. 1008 Decision Instituting IPR2014-01300 (Paper 8), Aug. 31, 2016.
Nu Mark LLC, IPR2016-01706, Ex. 1009 Certified Translation of CN 200620090805 (Chinese original included), Aug. 31, 2016.
Nu Mark LLC, IPR2016-01706, Ex. 1010 Claim Construction Order, *Fontem Ventures B.V. et al.* v. *NJOY, Inc. et al.*, Civil Action No. 2:14-cv-1645 (C.D. Cal.), Jan. 29, 2015 [DI-65], Aug. 31, 2016.
Nu Mark LLC, IPR2016-01706, Ex. 1011 Complaint, *Fontem Ventures B.V., et al.* v. *Nu Mark LLC*, Case No. 2:16-cv-04537 (excerpt), Aug. 31, 2016.
Nu Mark LLC, IPR2016-01706, Ex. 1012 U.S. Pat. No. 8,689,805 (the "805 Patent"), Aug. 31, 2016.
Nu Mark LLC, IPR2016-01706, Ex. 1013 File History for U.S. Appl. No. 13/426,817 (issued as U.S. Pat. No. 8,689,805) (excerpt), Aug. 31, 2016.
Nu Mark LLC, IPR2016-01706, Ex. 1014 Certified Translation of WO 2007/131450 (Chinese original included), Aug. 31, 2016.
Nu Mark LLC, IPR2016-01706, Ex. 1015 Patent Owner Prelim. Resp., *Logic Technology Development, LLC* v. *Fontem Holdings 1 B.V.*, IPR2015-00098, Paper 7 (Feb. 18, 2015), Aug. 31, 2016.
Nu Mark LLC, IPR2016-01706, Ex. 1016 U.S. Pat. App. Pub. No. 2009/0188490, Aug. 31, 2016.
Nu Mark LLC, IPR2016-01706, Ex. 1017 File History for U.S. Appl. No. 14/723,209 (the "209 Application") (issued as U.S. Pat. No. 9,326,551), Aug. 31, 2016.
Nu Mark LLC, Petition for Inter Partes Review of U.S. Pat. No. 9,326,551—IPR2017-00342, Paper 1 Petition, Nov. 28, 2016.
Nu Mark LLC, IPR2017-00342, Ex.1001 U.S. Pat. No. 9,326,551, Nov. 28, 2016.
Nu Mark LLC, IPR2017-00342, Ex.1002 File History for U.S. Pat. No. 9,326,551 (excerpts), Nov. 28, 2016.
Nu Mark LLC, IPR2017-00342, Ex.1003 Declaration of Dr. John Collins, Nov. 28, 2016.
Nu Mark LLC, IPR2017-00342, Ex.1004 U.S. Pat. No. 6,155,268 ("Takeuchi"), Nov. 28, 2016.
Nu Mark LLC, IPR2017-00342, Ex.1005 U.S. Pat. No. 2,057,353 ("Whittemore"), Nov. 28, 2016.
Nu Mark LLC, IPR2017-00342, Ex.1006 U.S. Pat. No. 4,947,874 ("Brooks"), Nov. 28, 2016.
Nu Mark LLC, IPR2017-00342, Ex.1007 European Patent Application No. EP0845220 BI ("Susa"), Nov. 28, 2016.
Nu Mark LLC, IPR2017-00342, Ex.1008 J.A. Speck, Mechanical Fastening, Joining, and Assembly (1997) (excerpt), Nov. 28, 2016.
Nu Mark LLC, IPR2017-00342, Ex.1009 McGraw-Hill Dictionary of Scientific and Technical Terms, McGraw-Hill Companies, Inc., (5th ed. 1994) (excerpt), Nov. 28, 2016.
Nu Mark LLC, IPR2017-00342, Ex.1010 U.S. Pat. No. 3,685,522 ("Kleinhans"), Nov. 28, 2016.
Nu Mark LLC, IPR2017-00342, Ex.1011 U.S. Patent Application No. 2006/0093977 AI ("Pellizzari I"), Nov. 28, 2016.
Nu Mark LLC, IPR2017-00342, Ex.1012 U.S. Pat. No. 7,059,307 ("Pellizzari II"), Nov. 28, 2016.
Nu Mark LLC, IPR2017-00342, Ex.1013 U.S. Pat. No. 3,200,819 ("Gilbert"), Nov. 28, 2016.
Nu Mark LLC, IPR2017-00342, Ex.1014 U.S. Pat. No. 5,894,841 ("Voges"), Nov. 28, 2016.
Nu Mark LLC, IPR2017-00342, Ex.1015 U.S. Pat. No. 5,743,251 ("Howell"), Nov. 28, 2016.
Nu Mark LLC, IPR2017-00342, Ex.1016 U.S. Pat. No. 2,461,664 ("Smith"), Nov. 28, 2016.
Nu Mark LLC, IPR2017-00342, Ex.1017 U.S. Pat. No. 3,234,357 ("Seuthe"), Nov. 28, 2016.
Nu Mark LLC, IPR2017-00342, Ex.1018 U.S. Pat. No. 5,745,985 ("Ghosh"), Nov. 28, 2016.
Nu Mark LLC, IPR2017-00342, Ex.1019 U.S. Pat. No. 4,676,237 ("Wood"), Nov. 28, 2016.
Nu Mark LLC, IPR2017-00342, Ex.1020 U.S. Patent No. 438,310 ("Edison"), Nov. 28, 2016.
Nu Mark LLC, IPR2017-00342, Ex.1021 U.S. Pat. No. 4,945,448 ("Bremenour"), Nov. 28, 2016.
Nu Mark LLC, IPR2017-00342, Ex.1022 R. Messler, Joining of Materials and Structures (2004), Nov. 28, 2016.
Nu Mark LLC, IPR2017-00342, Ex.1023 U.S. Pat. No. 2,442,004 ("Hayward-Butt"), Nov. 28, 2016.
Nu Mark LLC, IPR2017-00342, Ex.1024 U.S. Pat. No. 5,177,424 ("Connors"), Nov. 28, 2016.
Nu Mark LLC, IPR2017-00342, Ex.1025 U.S. Pat. No. 6,501,052 ("Cox"), Nov. 28, 2016.
Nu Mark LLC, IPR2017-00342, Ex.1026 U.S. Pat. No. 6,491,233 ("Nichols"), Nov. 28, 2016.
Nu Mark LLC, IPR2017-00342, Ex.1027 U.S. Pat. No. 1,084,304 ("Vaughn"), Nov. 28, 2016.
Nu Mark LLC, IPR2017-00342, Ex.1028 U.S. Pat. No. 5,266,746 ("Nishihara"), Nov. 28, 2016.

(56) References Cited

OTHER PUBLICATIONS

Nu Mark LLC, IPR2017-00342, Ex.1029 U.S. Pat. No. 4,968,263 ("Silbernagel"), Nov. 28, 2016.
Nu Mark LLC, IPR2017-00342, Ex.1030 U.S. Patent Application No. 2009/0126745 Al ("Hon"), Nov. 28, 2016.
Nu Mark LLC, IPR2017-00342, Ex.1031 European Patent Application No. EP1584910 Bl ("Hayato"), Nov. 28, 2016.
Nu Mark LLC, IPR2017-00342, Ex.1032 U.S. Pat. No. 6,311,561 ("Bang"), Nov. 28, 2016.
Nu Mark LLC, IPR2017-00342, Ex.1033 European Patent Publication No. EP 2 022 349 Al, Nov. 28, 2016.
Nu Mark LLC, IPR2017-00342, Ex.1034 *Nicocigs Limited* v. *Fontem Holdings 1 BV et al.*, British High Court of Justice, Approved Judgment (Sep. 2, 2016)., Nov. 28, 2016.
Nu Mark LLC, IPR2017-00342, Ex.1035 U.S. Patent Application No. 2004/0234916 Al ("Hale"), Nov. 28, 2016.
Nu Mark LLC, IPR2017-00342, Ex.1036 U.S. Pat. No. 4,922,901, Nov. 28, 2016.
Nu Mark LLC, IPR2017-00342, Ex.1037 Webster's Third New International Dictionary of the English Language, Merriam-Webster Inc. (1993) (excerpt), Nov. 28, 2016.
Nu Mark LLC, IPR2017-00342, Ex.1038 Invalidation Decision (No. WX15007), Patent Reexamination Board of the State Intellectual Property Office of the People's Republic of China (Jun. 13, 2010), with certified translation, Nov. 28, 2016.
Nu Mark LLC, IPR2017-00342, Ex.1039 Canadian Patent Application No. CA2752134 ("Hon 134"), Nov. 28, 2016.
Nu Mark LLC, Petition for Inter Partes Review of U.S. Pat. No. 9,339,062—IPR2016-01705, Paper 1 Petition, Aug. 31, 2016.
Nu Mark LLC, IPR2016-01705, Ex. 1001 U.S. Pat. No. 9,339,062 (the "062 Patent"), Aug. 31, 2016.
Nu Mark LLC, IPR2016-01705, Ex. 1002 File History for U.S. Appl. No. 13/754,521 (the "521 Application") (issued as U.S. Pat. No. 9,370,205) (excerpt), Aug. 31, 2016.
Nu Mark LLC, IPR2016-01705, Ex. 1003 Declaration of John M. Collins, Ph.D., Aug. 31, 2016.
Nu Mark LLC, IPR2016-01705, Ex. 1004 Curriculum Vitae of Dr. John M. Collins, Aug. 31, 2016.
Nu Mark LLC, IPR2016-01705, Ex. 1005 U.S. Pat. App. Pub. No. 2009/0126745 ("Hon 745"), Aug. 31, 2016.
Nu Mark LLC, IPR2016-01705, Ex. 1006 File History for U.S. Appl. No. 12/226,819 ("the 819 Application") (issued as U.S. Pat. No. 8,375,957) (excerpt), Aug. 31, 2016.
Nu Mark LLC, IPR2016-01705, Ex. 1007 U.S. Pat. No. 8,375,957 ("the 957 Patent"), Aug. 31, 2016.
Nu Mark LLC, IPR2016-01705, Ex. 1008 Decision Instituting IPR2014-01300 (Paper 8), Aug. 31, 2016.
Nu Mark LLC, IPR2016-01705, Ex. 1009 Certified Translation of CN 200620090805 (Chinese original included), Aug. 31, 2016.
Nu Mark LLC, IPR2016-01705, Ex. 1010 Claim Construction Order, *Fontem Ventures B.V. et al.* v. *NJOY, Inc. et al.*, Civil Action No. 2:14-cv-1645 (C.D. Cal.), Jan. 29, 2015 [DI-65], Aug. 31, 2016.
Nu Mark LLC, IPR2016-01705, Ex. 1011 Complaint, *Fontem Ventures B.V., et al.* v. *Nu Mark LLC*, Case No. 2:16-cv-04537 (excerpt), Aug. 31, 2016.
Nu Mark LLC, IPR2016-01705, Ex. 1012 U.S. Pat. No. 8,689,805 (the "805 Patent"), Aug. 31, 2016.
Nu Mark LLC, IPR2016-01705, Ex. 1013 File History for U.S. Appl. No. 13/426,817 (issued as U.S. Pat. No. 8,689,805) (excerpt), Aug. 31, 2016.
Nu Mark LLC, IPR2016-01705, Ex. 1014 Certified Translation of WO 2007/131450 (Chinese original included), Aug. 31, 2016.
Nu Mark LLC, IPR2016-01705, Ex. 1015 Patent Owner Prelim. Resp., *Logic Technology Development, LLC* v. *Fontem Holdings 1 B.V.*, IPR2015-00098, Paper 7 (Feb. 18, 2015), Aug. 31, 2016.
Nu Mark LLC, IPR2016-01705, Ex. 1016 U.S. Pat. App. Pub. No. 2009/0188490, Aug. 31, 2016.
Nu Mark LLC, IPR2016-01705, Ex. 1017 File History for U.S. Appl. No. 14/723,244 (the "244 Application") (issued as U.S. Pat. No. 9,339,062), Aug. 31, 2016.

Nu Mark LLC, Petition for Inter Partes Review of U.S. Pat. No. 9,339,062—IPR2017-00303, Paper 1 Petition, Nov. 18, 2016.
Nu Mark LLC, IPR2017-00303, Ex.1001 U.S. Pat. No. 9,339,062, Nov. 18, 2016.
Nu Mark LLC, IPR2017-00303, Ex.1002 File History for U.S. Pat. No. 9,339,062 (excerpts), Nov. 18, 2016.
Nu Mark LLC, IPR2017-00303, Ex.1003 Declaration of Dr. John Collins, Nov. 18, 2016.
Nu Mark LLC, IPR2017-00303, Ex.1004 U.S. Pat. No. 6,155,268 ("Takeuchi"), Nov. 18, 2016.
Nu Mark LLC, IPR2017-00303, Ex.1005 U.S. Pat. No. 2,057,353 ("Whittemore"), Nov. 18, 2016.
Nu Mark LLC, IPR2017-00303, Ex.1006 U.S. Pat. No. 4,947,874 ("Brooks"), Nov. 18, 2016.
Nu Mark LLC, IPR2017-00303, Ex.1007 European Patent Application No. EP0845220 Bl ("Susa"), Nov. 18, 2016.
Nu Mark LLC, IPR2017-00303, Ex.1008 J.A. Speck, Mechanical Fastening, Joining, and Assembly (1997) (excerpt), Nov. 18, 2016.
Nu Mark LLC, IPR2017-00303, Ex.1009 McGraw-Hill Dictionary of Scientific and Technical Terms, McGraw-Hill Companies, Inc., (6th ed. 2003) (excerpt), Nov. 18, 2016.
Nu Mark LLC, IPR2017-00303, Ex.1010 Invalidation Decision (No. WX15007), Patent ReexaminationBoard of the State Intellectual Property Office of the People's Republic of China (Jun. 13, 2010), with certified translation, Nov. 18, 2016.
Nu Mark LLC, IPR2017-00303, Ex.1011 U.S. Patent Application No. 2006/0093977 Al ("Pellizzari I"), Nov. 18, 2016.
Nu Mark LLC, IPR2017-00303, Ex.1012 U.S. Pat. No. 7,059,307 ("Pellizzari II"), Nov. 18, 2016.
Nu Mark LLC, IPR2017-00303, Ex.1013 U.S. Pat. No. 3,200,819 ("Gilbert"), Nov. 18, 2016.
Nu Mark LLC, IPR2017-00303, Ex.1014 U.S. Pat. No. 5,894,841 ("Voges"), Nov. 18, 2016.
Nu Mark LLC, IPR2017-00303, Ex.1015 U.S. Pat. No. 5,743,251 ("Howell"), Nov. 18, 2016.
Nu Mark LLC, IPR2017-00303, Ex.1016 U.S. Pat. No. 2,461,664 ("Smith"), Nov. 18, 2016.
Nu Mark LLC, IPR2017-00303, Ex.1017 U.S. Pat. No. 3,234,357 ("Seuthe"), Nov. 18, 2016.
Nu Mark LLC, IPR2017-00303, Ex.1018 U.S. Pat. No. 5,745,985 ("Ghosh"), Nov. 18, 2016.
Nu Mark LLC, IPR2017-00303, Ex.1019 U.S. Pat. No. 4,676,237 ("Wood"), Nov. 18, 2016.
Nu Mark LLC, IPR2017-00303, Ex.1020 U.S. Patent No. 438,310 ("Edison"), Nov. 18, 2016.
Nu Mark LLC, IPR2017-00303, Ex.1021 U.S. Pat. No. 4,945,448 ("Bremenour"), Nov. 18, 2016.
Nu Mark LLC, IPR2017-00303, Ex.1022 R. Messler, Joining of Materials and Structures (2004) (excerpt), Nov. 18, 2016.
Nu Mark LLC, IPR2017-00303, Ex.1023 U.S. Pat. No. 2,442,004 ("Hayward-Butt"), Nov. 18, 2016.
Nu Mark LLC, IPR2017-00303, Ex.1024 U.S. Pat. No. 5,177,424 ("Connors"), Nov. 18, 2016.
Nu Mark LLC, IPR2017-00303, Ex.1025 U.S. Pat. No. 6,501,052 ("Cox"), Nov. 18, 2016.
Nu Mark LLC, IPR2017-00303, Ex.1026 U.S. Pat. No. 6,491,233 ("Nichols"), Nov. 18, 2016.
Nu Mark LLC, IPR2017-00303, Ex.1027 U.S. Pat. No. 1,084,304 ("Vaughn"), Nov. 18, 2016.
Nu Mark LLC, IPR2017-00303, Ex.1028 U.S. Pat. No. 5,266,746 ("Nishihara"), Nov. 18, 2016.
Nu Mark LLC, IPR2017-00303, Ex.1029 U.S. Pat. No. 4,968,263 ("Silbernagel"), Nov. 18, 2016.
Nu Mark LLC, IPR2017-00303, Ex.1030 European Patent Application No. EP1584910 Bl ("Hayato"), Nov. 18, 2016.
Nu Mark LLC, IPR2017-00303, Ex.1031 U.S. Pat. No. 6,311,561 ("Bang"), Nov. 18, 2016.
Nu Mark LLC, IPR2017-00303, Ex.1032 *Nicocigs Limited* v. *Fontem Holdings 1 BV et al.*, British High Court of Justice, Approved Judgment (Sep. 2, 2016), Nov. 18, 2016.
Nu Mark LLC, Petition for Inter Partes Review of U.S. Pat. No. 9,339,062—IPR2017-00303, Ex. 1033 Canadian Patent Application No. CA2752134 ("Hon 134"), Nov. 18, 2016.

(56) References Cited

OTHER PUBLICATIONS

Nu Mark LLC, IPR2017-00303, Ex. 1034 U.S. Appl. No. 2009/0126745 Al ("Hon"), Nov. 18, 2016.
Nu Mark LLC, IPR2017-00303, Ex. 1035 European Patent Publication No. EP 2 022 349 Al, Nov. 18, 2016.
Nu Mark LLC, IPR2017-00303, Ex. 1036 U.S. Pat. No. 4,922,901 ("Brooks 901"), Nov. 18, 2016.
Nu Mark LLC, IPR2017-00303, Ex. 1037 U.S. Appl. No. 2004/0234916 Al ("Hale"), Nov. 18, 2016.
Nu Mark LLC, Petition for Inter Partes Review of U.S. Pat. No. 9,370,205—IPR2016-01642, Paper 1 Petition, Aug. 18, 2016.
Nu Mark LLC, IPR2016-01642, Ex. 1001 U.S. Pat. No. 9,370,205 (the "205 Patent"), Aug. 18, 2016.
Nu Mark LLC, IPR2016-01642, Ex. 1002 File History for U.S. Appl. No. 13/754,521 (the "521 Application") (issued as U.S. Pat. No. 9,370,205), Aug. 18, 2016.
Nu Mark LLC, IPR2016-01642, Ex. 1003 Declaration of John M. Collins, Ph.D., Aug. 18, 2016.
Nu Mark LLC, IPR2016-01642, Ex. 1004 Curriculum Vitae of Dr. John M. Collins, Aug. 18, 2016.
Nu Mark LLC, IPR2016-01642, Ex. 1005 U.S. Pat. App. Pub. No. 2009/0126745 ("Hon 745"), Aug. 18, 2016.
Nu Mark LLC, IPR2016-01642, Ex. 1006 File History for U.S. Appl. No. 12/226,819 ("The 819 Application") (issued as U.S. Pat. No. 8,375,957), Aug. 18, 2016.
Nu Mark LLC, IPR2016-01642, Ex. 1007 U.S. Pat. No. 8,375,957 ("the 957 Patent"), Aug. 18, 2016.
Nu Mark LLC, IPR2016-01642, Ex. 1008 Decision Instituting IPR2014-01300 (Paper 8), Aug. 18, 2016.
Nu Mark LLC, IPR2016-01642, Ex. 1009 Certified Translation of CN 200620090805 (Chinese original included), Aug. 18, 2016.
Nu Mark LLC, IPR2016-01642, Ex. 1010 Claim Construction Order, *Fontem Ventures B.V. et al.* v. *NJOY, Inc. et al.*, Civil Action No. 2:14-cv-1645 (C.D. Cal.), Jan. 29, 2015 [DI-65], Aug. 18, 2016.
Nu Mark LLC, IPR2016-01642, Ex. 1011 Complaint, *Fontem Ventures B.V., et al.* v. *Nu Mark LLC*, Case No. 2:16-cv-04537 (excerpt), Aug. 18, 2016.
Nu Mark LLC, IPR2016-01642, Ex. 1012 U.S. Pat. No. 8,689,805 (the "805 Patent"), Aug. 18, 2016.
Nu Mark LLC, IPR2016-01642, Ex. 1013 File History for U.S. Appl. No. 13/426,817 (issued as U.S. Pat. No. 8,689,805), Aug. 18, 2016.
Nu Mark LLC, IPR2016-01642, Ex. 1014 Certified Translation of WO 2007/131450 (Chinese original included), Aug. 18, 2016.
Nu Mark LLC, IPR2016-01642, Ex. 1015 Patent Owner Prelim. Resp., *Logic Technology Development, LLC* v. *Fontem Holdings 1 B.V.*, IPR2015-00098, Paper 7 (Feb. 18, 2015), Aug. 18, 2016.
Nu Mark LLC, IPR2016-01642, Ex. 1016 U.S. Pat. App. Pub. No. 2009/0188490, Aug. 18, 2016.
Nu Mark LLC, Petition for Inter Partes Review of U.S. Pat. No. 9,370,205—IPR2017-00257, Paper 1 Petition, Nov. 11, 2016.
Nu Mark LLC, IPR2017-00257, Ex.1001 U.S. Pat. No. 9,370,205, Nov. 11, 2016.
Nu Mark LLC, IPR2017-00257, Ex.1002 File History for U.S. Pat. No. 9,370,205 (excerpts), Nov. 11, 2016.
Nu Mark LLC, IPR2017-00257, Ex.1003 Declaration of Dr. John Collins, Nov. 11, 2016.
Nu Mark LLC, IPR2017-00257, Ex.1004 U.S. Pat. No. 6,155,268 ("Takeuchi"), Nov. 11, 2016.
Nu Mark LLC, IPR2017-00257, Ex.1005 U.S. Pat. No. 2,057,353 ("Whittemore"), Nov. 11, 2016.
Nu Mark LLC, IPR2017-00257, Ex.1006 U.S. Pat. No. 4,947,874 ("Brooks"), Nov. 11, 2016.
Nu Mark LLC, IPR2017-00257, Ex.1007 European Patent Application No. EP0845220 A1 ("Susa"), Nov. 11, 2016.
Nu Mark LLC, IPR2017-00257, Ex.1008 U.S. Pat. No. 4,922,901 ("Brooks 901"), Nov. 11, 2016.
Nu Mark LLC, IPR2017-00257, Ex.1009 McGraw-Hill Dictionary of Scientific and Technical Terms, McGraw-Hill Companies, Inc., (6th ed. 2003) (excerpt), Nov. 11, 2016.
Nu Mark LLC, IPR2017-00257, Ex.1010 U.S. Pat. No. 3,685,522 ("Kleinhans"), Nov. 11, 2016.
Nu Mark LLC, IPR2017-00257, Ex.1011 U.S. Patent Application No. 2006/0093977 A1 ("Pellizzari I"), Nov. 11, 2016.
Nu Mark LLC, IPR2017-00257, Ex.1012 U.S. Pat. No. 7,059,307 ("Pellizzari II"), Nov. 11, 2016.
Nu Mark LLC, IPR2017-00257, Ex.1013 U.S. Pat. No. 3,200,819 ("Gilbert"), Nov. 11, 2016.
Nu Mark LLC, IPR2017-00257, Ex.1014 U.S. Pat. No. 5,894,841 ("Voges"), Nov. 11, 2016.
Nu Mark LLC, IPR2017-00257, Ex.1015 U.S. Pat. No. 5,743,251 ("Howell"), Nov. 11, 2016.
Nu Mark LLC, IPR2017-00257, Ex.1016 U.S. Pat. No. 2,461,664 ("Smith"), Nov. 11, 2016.
Nu Mark LLC, IPR2017-00257, Ex.1017 U.S. Pat. No. 3,234,357 ("Seuthe"), Nov. 11, 2016.
Nu Mark LLC, IPR2017-00257, Ex.1018 U.S. Pat. No. 5,745,985 ("Ghosh"), Nov. 11, 2016.
Nu Mark LLC, IPR2017-00257, Ex.1019 U.S. Pat. No. 4,676,237 ("Wood"), Nov. 11, 2016.
Nu Mark LLC, IPR2017-00257, Ex.1020 U.S. Pat. No. 438,310 ("Edison"), Nov. 11, 2016.
Nu Mark LLC, IPR2017-00257, Ex.1021 U.S. Pat. No. 4,945,448 ("Bremenour"), Nov. 11, 2016.
Nu Mark LLC, IPR2017-00257, Ex.1022 R. Messler, Joining of Materials and Structures (2004) (excerpt), Nov. 11, 2016.
Nu Mark LLC, IPR2017-00257, Ex.1023 U.S. Pat. No. 2,442,004 ("Hayward-Butt"), Nov. 11, 2016.
Nu Mark LLC, IPR2017-00257, Ex.1024 U.S. Pat. No. 5,177,424 ("Connors"), Nov. 11, 2016.
Nu Mark LLC, IPR2017-00257, Ex.1025 U.S. Pat. No. 6,501,052 ("Cox"), Nov. 11, 2016.
Nu Mark LLC, IPR2017-00257, Ex.1026 U.S. Pat. No. 6,491,233 ("Nichols"), Nov. 11, 2016.
Nu Mark LLC, IPR2017-00257, Ex.1027 U.S. Pat. No. 1,084,304 ("Vaughn"), Nov. 11, 2016.
Nu Mark LLC, IPR2017-00257, Ex.1028 U.S. Pat. No. 5,266,746 ("Nishihara"), Nov. 11, 2016.
Nu Mark LLC, IPR2017-00257, Ex.1029 U.S. Pat. No. 4,968,263 ("Silbernagel"), Nov. 11, 2016.
Nu Mark LLC, IPR2017-00257, Ex.1030 U.S. Patent Application No. 2009/0126745 A1 ("Hon"), Nov. 11, 2016.
Nu Mark LLC, IPR2017-00257, Ex.1031 European Patent Application No. EP1584910 B1 ("Hayato"), Nov. 11, 2016.
Nu Mark LLC, IPR2017-00257, Ex.1032 U.S. Pat. No. 6,311,561 ("Bang"), Nov. 11, 2016.
Nu Mark LLC, IPR2017-00257, Ex.1033 European Patent Publication No. EP 2 022 349 A1, Nov. 11, 2016.
Nu Mark LLC, IPR2017-00257, Ex.1034 *Nicocigs Limited* v. *Fontem Holdings 1 BV et al.*, British High Court of Justice, Approved Judgment (Sep. 2, 2016)., Nov. 11, 2016.
Nu Mark LLC, IPR2017-00257, Ex.1035 U.S. Patent Application No. 2004/0234916 A1 ("Hale"), Nov. 11, 2016.
R.J. Reynolds Vapor Company, Petition for Inter Partes Review of U.S. Pat. No. 9,370,205—IPR2017-01641, Jun. 23, 2017.
R.J. Reynolds Vapor Company, IPR2017-01641, Exhibit 1001:U.S. Pat. No. 9,370,205, Jun. 23, 2017.
R.J. Reynolds Vapor Company, IPR2017-01641, Exhibit 1002:File History Excerpts for U.S. Pat. No. 9,370,205, Jun. 23, 2017.
R.J. Reynolds Vapor Company, IPR2017-01641, Exhibit 1003: Certified translation of WO 2007/131450 (with Chinese original included), Jun. 23, 2017.
R.J. Reynolds Vapor Company, IPR2017-01641, Exhibit 1004:U.S. Pat. No. 8,375,957, Jun. 23, 2017.
R.J. Reynolds Vapor Company, IPR2017-01641, Exhibit 1005:File History Excerpts for U.S. Pat. No. 8,375,957, Jun. 23, 2017.
R.J. Reynolds Vapor Company, IPR2017-01641, Exhibit 1006:Declaration of Robert Sturges, Ph.D., Jun. 23, 2017.
R.J. Reynolds Vapor Company, IPR2017-01641, Exhibit 1007:*Nu Mark, LLC* v. *Fontem Holdings 1 B.V.*, IPR2016-01642 (PTAB, filed Nov. 23, 2016), Paper No. 7, Jun. 23, 2017.
R.J. Reynolds Vapor Company, IPR2017-01641, Exhibit 1008: Translation of PCT/CN2007/001576, Jun. 23, 2017.

(56) References Cited

OTHER PUBLICATIONS

R.J. Reynolds Vapor Company, IPR2017-01641, Exhibit 1009:*Fontem Ventures B.V. et al.* v. *R.J. Reynolds Vapor Company,* No. 1:16-cv-04534 (M.D.N.C.), Document 1, Jun. 23, 2017.
R.J. Reynolds Vapor Company, IPR2017-01641, Exhibit 1010:U.S. Pat. No. 8,689,805, Jun. 23, 2017.
R.J. Reynolds Vapor Company, IPR2017-01641, Exhibit 1011:File History for U.S. Pat. No. 8,689,805, Jun. 23, 2017.
R.J. Reynolds Vapor Company, IPR2017-01641, Exhibit 1012:U.S. Pat. No. 8,720,320, Jun. 23, 2017.
R.J. Reynolds Vapor Company, Petition for Inter Partes Review of U.S. Pat. No. 9,370,205—IPR2017-01642, Jun. 26, 2017.
R.J. Reynolds Vapor Company, IPR2017-01642, Exhibit 1001:U.S. Pat. No. 9,370,205 to Lik Hon, Jun. 26, 2017.
R.J. Reynolds Vapor Company, IPR2017-01642, Exhibit 1002:U.S. Pat. No. 4,947,874 to Brooks et al., Jun. 26, 2017.
R.J. Reynolds Vapor Company, IPR2017-01642, Exhibit 1003:U.S. Pat. No. 2,057,353 to C. L. Whittemore, Jr., Jun. 26, 2017.
R.J. Reynolds Vapor Company, IPR2017-01642, Exhibit 1004:Declaration of Dr. Robert Sturges, Jun. 26, 2017.
R.J. Reynolds Vapor Company, IPR2017-01642, Exhibit 1005:*Nu Mark, LLC* v. *Fontem Holdings 1 B.V.,* IPR2017-00257 (PTAB, filed Nov. 11, 2016), Paper No. 10, Jun. 26, 2017.
R.J. Reynolds Vapor Company, IPR2017-01642, Exhibit 1006:U.S. Appl. No. 13/754,521, filed Jan. 30, 2012, Jun. 26, 2017.
R.J. Reynolds Vapor Company, IPR2017-01642, Exhibit 1007:Model No. MPL-502-V by Micro Pneumatic Logic, annotated image of pressure sensing port, Jun. 26, 2017.
R.J. Reynolds Vapor Company, IPR2017-01642, Exhibit 1008:Model No. MPL-502-V by Micro Pneumatic Logic, annotated image of pressure balancing port, Jun. 26, 2017.
R.J. Reynolds Vapor Company, IPR2017-01642, Exhibit 1009:MPL 502 Series Specifications, Micro Pneumatic Logic, Inc., (Mar. 11, 2006), http://www.pressureswitch.com/PDFs/0502STANDARDA.pdf [https://web.archive.org/web/20060311132848/http://www.pressureswitch.com/PDFs/0502STANDARDA.pdf], Jun. 26, 2017.
R.J. Reynolds Vapor Company, IPR2017-01642, Exhibit 1010:MPL Pressure Switch Solutions, Micro Pneumatic Logic, Inc., (Mar. 11, 2006), http://www.pressureswitch.com/PDFs/2000_MPLBrochure.pdf [https://web.archive.org/web/20060311132419/http://www.pressureswitch.com/PDFs/2000_MPLBrochure.pdf], Jun. 26, 2017.
R.J. Reynolds Vapor Company, IPR2017-01642, Exhibit 1011:McGraw-Hill Dictionary of Scientific and Technical Terms, McGraw-Hill Companies, Inc. (6th ed. 2003) (excerpt), Jun. 26, 2017.
R.J. Reynolds Vapor Company, IPR2017-01642, Exhibit 1012:*Nu Mark, LLC* v. *Fontem Holdings 1 B.V.,* IPR2016-01642 (PTAB, filed Aug. 18, 2016), Paper No. 7, Jun. 26, 2017.
R.J. Reynolds Vapor Company, IPR2017-01642, Exhibit 1013:*Nu Mark, LLC* v. *Fontem Holdings 1 B.V.,* IPR2016-01283 (PTAB, filed Jun. 28, 2016), Paper No. 12, Jun. 26, 2017.
R.J. Reynolds Vapor Company, IPR2017-01642, Exhibit 1014:U.S. Pub. No. 2009/0126745 to Hon, which is the parent application publication of the 205 patent (Ex.1001), Jun. 26, 2017.
R.J. Reynolds Vapor Company, IPR2017-01642, Exhibit 1015:U.S. Pat. No. 3,685,522 to Kleinhans, Jun. 26, 2017.
R.J. Reynolds Vapor Company, IPR2017-01642, Exhibit 1016:U.S. Pat. No. 4,637,407 to Bonanno et al., Jun. 26, 2017.
R.J. Reynolds Vapor Company, IPR2017-01642, Exhibit 1017:U.S. Pat. No. 5,266,746 to Nishihara et al., Jun. 26, 2017.
R.J. Reynolds Vapor Company, IPR2017-01642, Exhibit 1018:U.S. Pat. No. 4,968,263 to Silbernagel et al., Jun. 26, 2017.
R.J. Reynolds Vapor Company, IPR2017-01642, Exhibit 1019:U.S. Pat. No. 2,461,664 to Smith, Jun. 26, 2017.
R.J. Reynolds Vapor Company, IPR2017-01642, Exhibit 1020:U.S. Pat. No. 3,234,357 to Seuthe, Jun. 26, 2017.
R.J. Reynolds Vapor Company, IPR2017-01642, Exhibit 1021:U.S. Pat. No. 5,743,251 to Howell et al., Jun. 26, 2017.
R.J. Reynolds Vapor Company, IPR2017-01642, Exhibit 1022:Chinese Pat. No. 2719043Y to Lik Hon, Jun. 26, 2017.
R.J. Reynolds Vapor Company, IPR2017-01642, Exhibit 1023:Certified English translation of Chinese Pat. No. 2719043Y to Lik Hon, Jun. 26, 2017.
R.J. Reynolds Vapor Company, IPR2017-01642, Exhibit 1024:U.S. Pat. No. 6,598,607 to Adiga et al., Jun. 26, 2017.
R.J. Reynolds Vapor Company, IPR2017-01642, Exhibit 1025:U.S. Pat. No. 4,793,365 to Sensabaugh, Jr. et al., Jun. 26, 2017.
R.J. Reynolds Vapor Company, IPR2017-01642, Exhibit 1026:U.S. Pat. No. 5,203,355 to Clearman et al., Jun. 26, 2017.
R.J. Reynolds Vapor Company, IPR2017-01642, Exhibit 1027:U.S. Pat. No. 2,472,282 to Burchett, Jun. 26, 2017.
R.J. Reynolds Vapor Company, IPR2017-01642, Exhibit 1028:U.S. Pat. No. 2,032,695 to Gimera at al., Jun. 26, 2017.
R.J. Reynolds Vapor Company, IPR2017-01642, Exhibit 1029:U.S. Pat. No. 5,703,633 to Gehrer et al., Jun. 26, 2017.
R.J. Reynolds Vapor Company, IPR2017-01642, Exhibit 1030:U.S. Pat. No. 6,885,814 to Saito et al., Jun. 26, 2017.
R.J. Reynolds Vapor Company, IPR2017-01642, Exhibit 1031:U.S. Pat. No. 5,894,841 to Voges, Jun. 26, 2017.
R.J. Reynolds Vapor Company, IPR2017-01642, Exhibit 1032:European Pat. No. 1584910 to Tohyama et al., Jun. 26, 2017.
R.J. Reynolds Vapor Company, IPR2017-01642, Exhibit 1033:U.S. Pat. No. 6,311,561 to Bang et al., Jun. 26, 2017.
R.J. Reynolds Vapor Company, IPR2017-01642, Exhibit 1034:U.S. Pat. No. 2,442,004 to Hayward-Butt, Jun. 26, 2017.
R.J. Reynolds Vapor Company, IPR2017-01642, Exhibit 1035:U.S. Pat. No. 3,200,819 to Gilbert, Jun. 26, 2017.
R.J. Reynolds Vapor Company, IPR2017-01642, Exhibit 1036:U.S. Pat. No. 6,155,268 to Takeuchi, Jun. 26, 2017.
R.J. Reynolds Vapor Company, IPR2017-01642, Exhibit 1037:U.S. Pat. No. 5,745,985 to Ghosh, Jun. 26, 2017.
R.J. Reynolds Vapor Company, IPR2017-01642, Exhibit 1038:U.S. Pat. No. 4,676,237 to Wood, Jun. 26, 2017.
R.J. Reynolds Vapor Company, IPR2017-01642, Exhibit 1039:U.S. Pat. No. 4,945,448 to Bremenour, Jun. 26, 2017.
R.J. Reynolds Vapor Company, IPR2017-01642, Exhibit 1040:R. Messier, Joining of Materials and Structures (2004) (excerpt), Jun. 26, 2017.
R.J. Reynolds Vapor Company, IPR2017-01642, Exhibit 1041:U.S. Pat. No. 438,310 to Edison, Jun. 26, 2017.
R.J. Reynolds Vapor Company, IPR2017-01642, Exhibit 1042:European Pat. Appl. No. EP0845220 A1 to Susa, Jun. 26, 2017.
R.J. Reynolds Vapor Company, IPR2017-01642, Exhibit 1043:U.S. Pat. No. 5,177,424 to Connors, Jun. 26, 2017.
R.J. Reynolds Vapor Company, IPR2017-01642, Exhibit 1044:U.S. Pat. No. 1,084,304 to Vaughn, Jun. 26, 2017.
R.J. Reynolds Vapor Company, IPR2017-01642, Exhibit 1045:*R.J. Reynolds Vapor Company* v. *Fontem Holdings 1 B.V.,* IPR2016-01270 (PTAB, filed Jul. 2, 2016), Paper No. 13, Jun. 26, 2017.
R.J. Reynolds Vapor Company, IPR2017-01642, Exhibit 1046: *R.J. Reynolds Vapor Company* v. *Fontem Holdings 1 B.V.,* IPR2016-01270 (PTAB, filed Jul. 2, 2016), Paper No. 11, Jun. 26, 2017.
R.J. Reynolds Vapor Company, IPR2017-01642, Exhibit 1047:European Pat No. EP 2,022,349 to Han, Jun. 26, 2017.
R.J. Reynolds Vapor Company, IPR2017-01642, Exhibit 1048:European Pat. Pub. 0 501 419 to Patteri, Jun. 26, 2017.
R.J. Reynolds Vapor Company, IPR2017-01642, Exhibit 1049:Merriam-Webster's Collegiate Dictionary, Merriam-Webster, Inc. (11th ed. 2003)(excerpt), Jun. 26, 2017.
R.J. Reynolds Vapor Company, IPR2017-01642, Exhibit 1050:Declaration of Kyle Yarberry, Jun. 26, 2017.
R.J. Reynolds Vapor Company, IPR2017-01642, Exhibit 1051:Record of purchase of MPL-502-V-G-Range-A sensor, Jun. 26, 2017.
R.J. Reynolds Vapor Company, IPR2017-01642, Exhibit 1052:U.S. Pat. No. 6,217,315 to Mifune et al., Jun. 26, 2017.
R.J. Reynolds Vapor Company, IPR2017-01642, Exhibit 1053:MPL 500: Low Pressure Momentary Switches, http://www.pryde.com.au/Data_Sheets/Industrial/02/MPL/MPL_500_pg1.pdf (last visited Jun. 26, 2017), Jun. 26, 2017.
R.J. Reynolds Vapor Company, IPR2017-01642, Exhibit 1055:*NuMark, LLC* v. *Fontem Holdings 1 B.V.,* IPR2017-00257 (PTAB, filed Dec. 9, 2016), Paper No. 10, Jun. 26, 2017.

(56) References Cited

OTHER PUBLICATIONS

R.J. Reynolds Vapor Company, Petition for Inter Partes Review of U.S. Pat. No. 8,375,957—IPR2018-00626, Mar. 2, 2018.
R.J. Reynolds Vapor Company, IPR2018-00626, Ex. 1001: U.S. Pat. No. 8,375,957 ("the 957 Patent"), Mar. 2, 2018.
R.J. Reynolds Vapor Company, IPR2018-00626, Ex. 1002: Declaration of Dr. Robert H. Sturges regarding U.S. Pat. No. 8,375,957, Mar. 2, 2018.
R.J. Reynolds Vapor Company, IPR2018-00626, Ex. 1003: U.S. Pat. No. 4,947,874 ("Brooks"), Mar. 2, 2018.
R.J. Reynolds Vapor Company, IPR2018-00626, Ex. 1004: U.S. Pat. No. 2,057,353 ("Whittemore"), Mar. 2, 2018.
R.J. Reynolds Vapor Company, IPR2018-00626, Ex. 1005: Institution Decision at 10-13 dated Jan. 4, 2017 (Paper 11), *R.J. Reynolds Vapor Company* v. *Fontem Holdings 1 B.V.*, IPR2016-01270 (PTAB, petition filed Jul. 2, 2016), Mar. 2, 2018.
R.J. Reynolds Vapor Company, IPR2018-00626, Ex. 1007: Order Dismissing Petition for Inter Partes Review dated May 11, 2015 (Paper 8), *Logic Technology Development, LLC*, v. *Fontem Holdings 1 B.V.*, Case No. IPR2015-00098, (PTAB, petition filed Oct. 21, 2014), Mar. 2, 2018.
R.J. Reynolds Vapor Company, IPR2018-00626, Ex. 1008: Order Dismissing Petition for Inter Partes Review dated Dec. 23, 2016 (Paper 12), *Nu Mark LLC.* v. *Fontem Holdings 1 B.V.*, IPR2016-01307 (PTAB, petition filed Jun. 28, 2016), Mar. 2, 2018.
R.J. Reynolds Vapor Company, IPR2018-00626, Ex. 1009: U.S. Pat. No. 1,517,584 ("Reece"), Mar. 2, 2018.
R.J. Reynolds Vapor Company, IPR2018-00626, Ex. 1010: U.S. Pat. No. 780,087 ("Burt").
R.J. Reynolds Vapor Company, IPR2018-00626, Ex. 1011: U.S. Pat. No. 2,959,664 ("Fenn"), Mar. 2, 2018.
R.J. Reynolds Vapor Company, IPR2018-00626, Ex. 1012: U.S. Pat. No. 2,086,192 ("Schumaker"), Mar. 2, 2018.
R.J. Reynolds Vapor Company, IPR2018-00626, Ex. 1013: U.S. Pat. No. 7,337,782 ("Thompson"), Mar. 2, 2018.
R.J. Reynolds Vapor Company, IPR2018-00626, Ex. 1014: McGraw-Hill Dictionary of Scientific and Technical Terms (Sybil P. Parker ed., 5th ed. 1994) (excerpt), Mar. 2, 2018.
R.J. Reynolds Vapor Company, IPR2018-00626, Ex. 1015: U.S. Pat. No. 4,941,486 ("Dube"), Mar. 2, 2018.
R.J. Reynolds Vapor Company, IPR2018-00626, Ex. 1016: European Patent Application Publ. EP 0 845 220 A1 ("Susa"), Mar. 2, 2018.
R.J. Reynolds Vapor Company, IPR2018-00626, Ex. 1017: Examination Decision on the Request for Declaration of Invalidity re: App. No. 200620090805.0 dated Jun. 23, 2010 (Document 2010061800220090) (State Intellectual Property Office of the People's Republic of China), Mar. 2, 2018.
R.J. Reynolds Vapor Company, IPR2018-00626, Ex. 1018: U.S. Pat. No. 438,310 ("Edison"), Mar. 2, 2018.
R.J. Reynolds Vapor Company, IPR2018-00626, Ex. 1019: U.S. Pat. No. 3,200,819 ("Gilbert"), Mar. 2, 2018.
R.J. Reynolds Vapor Company, IPR2018-00626, Ex. 1020: PCT International Application Publication No. WO/0028843 ("Pienemann"), Mar. 2, 2018.
R.J. Reynolds Vapor Company, IPR2018-00626, Ex. 1021: Certified Translation of PCT International Application Publication No. WO/0028843 ("Pienemann"), Mar. 2, 2018.
R.J. Reynolds Vapor Company, IPR2018-00626, Ex. 1022: Robert W. Messler, Jr., Joining of Materials and Structures—From Pragmatic Process to Enabling Technology (2004), Mar. 2, 2018.
R.J. Reynolds Vapor Company, IPR2018-00626, Ex. 1023: U.S. Pat. No. 5,894,841 ("Voges"), Mar. 2, 2018.
R.J. Reynolds Vapor Company, IPR2018-00626, Ex. 1024: James A. Speck, Mechanical Fastening, Joining, and Assembly (1997) (excerpts), Mar. 2, 2018.
R.J. Reynolds Vapor Company, IPR2018-00626, Ex. 1025: U.S. Pat. No. 6,155,268 ("Takeuchi"), Mar. 2, 2018.
R.J. Reynolds Vapor Company, IPR2018-00626, Ex. 1026: U.S. Pat. No. 4,922,901 ("Brooks 2"), Mar. 2, 2018.
R.J. Reynolds Vapor Company, IPR2018-00626, Ex. 1027: U.S. Pat. No. 2,461,664 ("Smith"), Mar. 2, 2018.
R.J. Reynolds Vapor Company, IPR2018-00626, Ex. 1028: U.S. Pat. No. 3,234,357 ("Seuthe"), Mar. 2, 2018.
R.J. Reynolds Vapor Company, IPR2018-00626, Ex. 1029: U.S. Pat. No. 1,084,304 ("Vaughn"), Mar. 2, 2018.
R.J. Reynolds Vapor Company, IPR2018-00626, Ex. 1030: U.S. Pat. No. 5,743,251 ("Howell"), Mar. 2, 2018.
R.J. Reynolds Vapor Company, IPR2018-00626, Ex. 1031: U.S. Pat. No. 6,217,315 ("Mifune"), Mar. 2, 2018.
R.J. Reynolds Vapor Company, IPR2018-00626, Ex. 1032: U.S. Pat. No. 5,266,746 ("Nishihara"), Mar. 2, 2018.
R.J. Reynolds Vapor Company, IPR2018-00626, Ex. 1033: U.S. Pat. No. 4,968,263 ("Silbernagel"), Mar. 2, 2018.
R.J. Reynolds Vapor Company, IPR2018-00626, Ex. 1034: U.S. Pat. No. 3,860,012 ("Selke"), Mar. 2, 2018.
R.J. Reynolds Vapor Company, IPR2018-00626, Ex. 1035: U.S. Pat. No. 2,442,004 ("Hayward-Butt"), Mar. 2, 2018.
R.J. Reynolds Vapor Company, IPR2018-00626, Ex. 1036: U.S. Pat. No. 6,598,607 ("Adiga"), Mar. 2, 2018.
R.J. Reynolds Vapor Company, IPR2018-00626, Ex. 1037: U.S. Pat. No. 4,793,365 ("Sensabaugh"), Mar. 2, 2018.
R.J. Reynolds Vapor Company, IPR2018-00626, Ex. 1038: U.S. Pat. No. 2,472,282 ("Burchett"), Mar. 2, 2018.
R.J. Reynolds Vapor Company, IPR2018-00626, Ex. 1039: U.S. Pat. No. 2,032,695 ("Gimera"), Mar. 2, 2018.
R.J. Reynolds Vapor Company, IPR2018-00626, Ex. 1040: U.S. Pat. No. 5,745,985 ("Ghosh"), Mar. 2, 2018.
R.J. Reynolds Vapor Company, IPR2018-00626, Ex. 1041: U.S. Pat. No. 4,676,237 ("Wood"), Mar. 2, 2018.
R.J. Reynolds Vapor Company, IPR2018-00626, Ex. 1042: U.S. Pat. No. 4,945,448 ("Bremenour"), Mar. 2, 2018.
R.J. Reynolds Vapor Company, IPR2018-00626, Ex. 1043: European Pat. No. 1584910 ("Tohyama"), Mar. 2, 2018.
R.J. Reynolds Vapor Company, IPR2018-00626, Ex. 1044: U.S. Pat. No. 6,311,561 ("Bang"), Mar. 2, 2018.
R.J. Reynolds Vapor Company, IPR2018-00626, Ex. 1045: U.S. Pat. No. 5,177,424 ("Connors"), Mar. 2, 2018.
R.J. Reynolds Vapor Company, IPR2018-00626, Ex. 1046: U.S. Pat. Pub. No. 2004/0234916 ("Hale"), Mar. 2, 2018.
R.J. Reynolds Vapor Company, IPR2018-00626, Ex. 1047: Information Disclosure Statements from File History for U.S. Pat. No. 8,375,957, Mar. 2, 2018.
R.J. Reynolds Vapor Company, IPR2018-00626, Ex. 1048: Chinese Pat. No. 2719043Y ("Hon 043"), Mar. 2, 2018.
R.J. Reynolds Vapor Company, IPR2018-00626, Ex. 1049: Merriam-Webster's Collegiate Dictionary (11th ed. 2003)—Excerpt, Mar. 2, 2018.
R.J. Reynolds Vapor Company, IPR2018-00626, Ex. 1050: Patent Owner Preliminary Response to Petition for Inter Partes Review dated Oct. 29, 2015 (Paper 5), *JT International S.A.* v. *Fontem Holdings 1 B.V.*, IPR2015-01604 (PTAB, petition filed Jul. 20, 2015), Mar. 2, 2018.
R.J. Reynolds Vapor Company, IPR2018-00626, Ex. 1051: Patent Owner Preliminary Response to Petition for Inter Partes Review dated Oct. 20, 2015 (Paper 8), *JT International S.A.* v. *Fontem Holdings 1 B.V.*, IPR2015-01513 (PTAB, petition filed Jun. 26, 2015), Mar. 2, 2018.
R.J. Reynolds Vapor Company, IPR2018-00626, Ex. 1052: Declaration of Kyle Yarberry, Mar. 2, 2018.
R.J. Reynolds Vapor Company, IPR2018-00626, Ex. 1053: U.S. Pat. No. 3,292,635 ("Kolodny"), Mar. 2, 2018.
R.J. Reynolds Vapor Company, IPR2018-00626, Ex. 1054: U.S. Pat. No. 3,685,521 ("Dock"), Mar. 2, 2018.
R.J. Reynolds Vapor Company, Petition for Inter Partes Review of U.S. Pat. No. 8,863,752—IPR2018-00628, Mar. 1, 2018.
R.J. Reynolds Vapor Company, IPR2018-00628, Ex. 1001 U.S. Pat. No. 8,863,752, Mar. 1, 2018.
R.J. Reynolds Vapor Company, IPR2018-00628, Ex. 1002, International Publication No. WO/28843 ("Pienemann"), Mar. 1, 2018.
R.J. Reynolds Vapor Company, IPR2018-00628, Ex. 1003: Certified Translation of International Publication No. WO/28843 ("Pienemann"), Mar. 1, 2018.

(56) References Cited

OTHER PUBLICATIONS

R.J. Reynolds Vapor Company, IPR2018-00628, Ex. 1004; U.S. Pat. No. 2,057,353 ("Whittemore"), Mar. 1, 2018.
R.J. Reynolds Vapor Company, IPR2018-00628, Ex. 1005: Declaration of Dr. Robert H. Sturges regarding U.S. Pat. No. 8,863,752, Mar. 1, 2018.
R.J. Reynolds Vapor Company, IPR2018-00628, Ex. 1006: Petition ofr Inter Partes Review dated Jul. 20, 2015 (Paper 1), *JT Int'l S.A. v. Fontem Holdings 1 B.V.*, IPR2015-01604 (P.T.A.B., petition filed Jul. 20, 2015), Mar. 1, 2018.
R.J. Reynolds Vapor Company, IPR2018-00628, Ex. 1007: Order Dismissing Petition for Inter Partes Review dated Dec. 14, 2015 (Paper 9), *JT Int'l S.A. v. Fontem Holdings 1 B.V.*, IPR2015-01604 (P.T.A.B., petition filed Jul. 20, 2015) (Please note, this Exhibit also applies to IPR2015-01513, IPR2015-01578, and IPR2015-01587), Mar. 1, 2018.
R.J. Reynolds Vapor Company, IPR2018-00628, Ex. 1008: Exhibit A to Parties' Joint Claim Construction Statement, *Fontem Ventures B.V. et al. v. R.J. Reynolds Vapor Company*, No. 1:16-cv-01255 (M.D.N.C.) (excerpts), Mar. 1, 2018.
R.J. Reynolds Vapor Company, IPR2018-00628, Ex. 1009: Declaration of Richard Meyst in Support of Patent Owner Preliminary Response to Petition for Inter Partes Review dated Sep. 30, 2016 (Ex. 2001), *Nu Mark LLC v. Fontem Holdings 1 B.V.*, IPR2016-01309 (P.T.A.B., petition filed Jun. 28, 2016), Mar. 1, 2018.
R.J. Reynolds Vapor Company, IPR2018-00628, Ex. 1010: Transcript of the Jul. 21, 2017 Deposition of Richard Meyst (Ex. 1029), *R.J. Reynolds Vapor Co. v. Fontem Holdings 1 B.V.*, IPR2016-01692 (P.T.A.B., petition filed Aug. 30, 2016), Mar. 1, 2018.
R.J. Reynolds Vapor Company, IPR2018-00628, Ex. 1011: Patent Owner's Preliminary Response dated Sep. 11, 2015 (Paper 7), *NJOY, Inc., et al. v. Fontem Holdings 1 B.V.*, IPR2015-01301 (P.T.A.B., petition filed May 29, 2015), Mar. 1, 2018.
R.J. Reynolds Vapor Company, IPR2018-00628, Ex. 1012: Patent Owner Preliminary Response to Petition for Inter Partes Review dated Sep. 30, 2016 (Paper 8), *Nu Mark LLC v. Fontem Holdings 1 B.V.*, IPR2016-01309 (P.T.A.B., petition filed Jun. 28, 2016), Mar. 1, 2018.
R.J. Reynolds Vapor Company, IPR2018-00628, Ex. 1013: Patent Owner Preliminary Response to Petition for Inter Partes Review dated Oct. 29, 2015 (Paper 5), *JT Int'l S.A. v. Fontem Holdings 1 B.V.*, IPR2015-01604 (P.T.A.B., petition filed Jul. 20, 2015), Mar. 1, 2018.
R.J. Reynolds Vapor Company, IPR2018-00628, Ex. 1014: Patent Owner Preliminary Response to Petition for Inter Partes Review dated Oct. 20, 2015 (Paper 8), *JT Int'l S.A. v. Fontem Holdings 1 B.V.*, IPR2015-01513 (P.T.A.B., petition filed Jun. 26, 2015), Mar. 1, 2018.
R.J. Reynolds Vapor Company, IPR2018-00628, Ex. 1015: U.S. Pat. No. 5,743,251 ("Howell"), Mar. 1, 2018.
R.J. Reynolds Vapor Company, IPR2018-00628, Ex. 1016: U.S. Pat. No. 3,428,053 ("Schoenbaum"), Mar. 1, 2018.
R.J. Reynolds Vapor Company, IPR2018-00628, Ex. 1017: U.S. Pat. No. 3,860,012 ("Selke"), Mar. 1, 2018.
R.J. Reynolds Vapor Company, IPR2018-00628, Ex. 1018: U.S. Pat. No. 4,270,552 ("Jenkins"), Mar. 1, 2018.
R.J. Reynolds Vapor Company, IPR2018-00628, Ex. 1019: U.S. Pat. No. 4,589,428 ("Keritsis"), Mar. 1, 2018.
R.J. Reynolds Vapor Company, IPR2018-00628, Ex. 1020: European Patent Application Publ. EP 0 845 220 A1 ("Susa"), Mar. 1, 2018.
R.J. Reynolds Vapor Company, IPR2018-00628, Ex. 1021: Decision Denying Institution of Inter Partes Review dated Dec. 9, 2015 (Paper 15), *NJOY, Inc., et al. v. Fontem Holdings 1 B.V.*, IPR2015-01302 (P.T.A.B., petition filed May 29, 2015), Mar. 1, 2018.
R.J. Reynolds Vapor Company, IPR2018-00628, Ex. 1022: Decision Granting Institution of Inter Partes Review dated Feb. 19, 2015 (Paper 8), *NJOY, Inc. v. Fontem Holdings 1 B.V.*, IPR2014-01289 (P.T.A.B., petition filed Aug. 14, 2014), Mar. 1, 2018.
R.J. Reynolds Vapor Company, IPR2018-00628, Ex. 1023: Decision Denying Institution of Inter Partes Review dated Dec. 23, 2016 (Paper 12), *Nu Mark LLC v. Fontem Holdings 1 B.V.*, IPR2016-01307 (P.T.A.B., petition filed Jun. 28, 2016), Mar. 1, 2018.
R.J. Reynolds Vapor Company, IPR2018-00628, Ex. 1024: U.S. Pat. No. 4,947,874 ("Brooks"), Mar. 1, 2018.
R.J. Reynolds Vapor Company, IPR2018-00628, Ex. 1025: U.S. Pat. No. 2,461,664 ("Smith"), Mar. 1, 2018.
R.J. Reynolds Vapor Company, IPR2018-00628, Ex. 1026: Merriam-Webster's Collegiate Dictionary, Merriam-Webster, Inc. (11th ed. 2003) (excerpts), Mar. 1, 2018.
R.J. Reynolds Vapor Company, IPR2018-00628, Ex. 1027: G.B. Patent No. 1,171,878 ("Selke 2"), Mar. 1, 2018.
R.J. Reynolds Vapor Company, IPR2018-00628, Ex. 1028: U.S. Pat. No. 1,879,128 ("McKee"), Mar. 1, 2018.
R.J. Reynolds Vapor Company, IPR2018-00628, Ex. 1029: U.S. Pat. No. 2,959,664 ("Fenn"), Mar. 1, 2018.
R.J. Reynolds Vapor Company, IPR2018-00628, Ex. 1030: U.S. Pat. No. 2,269,394 ("Cuno"), Mar. 1, 2018.
R.J. Reynolds Vapor Company, IPR2018-00628, Ex. 1031: Declaration of Kyle E. Yarberry, Mar. 1, 2018.
R.J. Reynolds Vapor Company, Petition for Inter Partes Review of U.S. Pat. No. 9,339,062—IPR2018-00631, Mar. 2, 2018.
R.J. Reynolds Vapor Company, IPR2018-00631, Ex. 1001: U.S. Pat. No. 9,339,062 ("the 062 Patent"), Mar. 2, 2018.
R.J. Reynolds Vapor Company, IPR2018-00631, Ex. 1002: Declaration of Dr. Robert H. Sturges regarding U.S. Pat. No. 9,339,062, Mar. 2, 2018.
R.J. Reynolds Vapor Company, IPR2018-00631, Ex. 1003: U.S. Pat. No. 4,947,874 ("Brooks"), Mar. 2, 2018.
R.J. Reynolds Vapor Company, IPR2018-00631, Ex. 1004: U.S. Pat. No. 2,057,353 ("Whittemore"), Mar. 2, 2018.
R.J. Reynolds Vapor Company, IPR2018-00631, Ex. 1005: U.S. Pat. No. 5,177,424 ("Connors"), Mar. 2, 2018.
R.J. Reynolds Vapor Company, IPR2018-00631, Ex. 1006: File History for U.S. Pat. No. 9,339,062 (excerpts), Mar. 2, 2018.
R.J. Reynolds Vapor Company, IPR2018-00631, Ex. 1007: Termination Order dated Jan. 4, 2017 (Paper 9), *Nu Mark LLC v. Fontem Holdings 1 B.V.*, IPR2017-00342 (P.T.A.B., petitioned filed Nov. 28, 2016) (please note, that termination order was first entered in IPR2016-1288, but applied to IPR2017-00342), Mar. 2, 2018.
R.J. Reynolds Vapor Company, IPR2018-00631, Ex. 1008: Institution Decision dated Dec. 23, 2016 (Paper 12), *Nu Mark LLC. v. Fontem Holdings 1 B.V.*, IPR2016-01307 (P.T.A.B., petition filed Jun. 28, 2016), Mar. 2, 2018.
R.J. Reynolds Vapor Company, IPR2018-00631, Ex. 1009: U.S. Pat. No. 1,517,584 ("Reece"), Mar. 2, 2018.
R.J. Reynolds Vapor Company, IPR2018-00631, Ex. 1010: U.S. Pat. No. 780,087 ("Burt"), Mar. 2, 2018.
R.J. Reynolds Vapor Company, IPR2018-00631, Ex. 1011: U.S. Pat. No. 2,959,664 ("Fenn"), Mar. 2, 2018.
R.J. Reynolds Vapor Company, IPR2018-00631, Ex. 1012: U.S. Pat. No. 2,086,192 ("Schumaker"), Mar. 2, 2018.
R.J. Reynolds Vapor Company, IPR2018-00631, Ex. 1013: Institution Decision dated Mar. 13, 2017 (Paper 8), *R.J. Reynolds Vapor Company v. Fontem Holdings 1 B.V.*, IPR2016-01859 (P.T.A.B., petition filed Sep. 23, 2016), Mar. 2, 2018.
R.J. Reynolds Vapor Company, IPR2018-00631, Ex. 1014: McGraw-Hill Dictionary of Scientific and Technical Terms (Sybil P. Parker ed., 5th ed. 1994) (excerpts), Mar. 2, 2018.
R.J. Reynolds Vapor Company, IPR2018-00631, Ex. 1015: The Oxford American Dictionary and Thesaurus with Language Guide (2003) (excerpts), Mar. 2, 2018.
R.J. Reynolds Vapor Company, IPR2018-00631, Ex. 1016: Random House Webster's Unabridged Dictionary (2nd ed. 2001) (excerpts), Mar. 2, 2018.
R.J. Reynolds Vapor Company, IPR2018-00631, Ex. 1017: Institution Decision dated Nov. 30, 2016 (Paper 12), *Nu Mark LLC v. Fontem Holdings 1 B.V.*, IPR2016-01283 (P.T.A.B., petition filed Jun. 28, 2016), Mar. 2, 2018.

(56) References Cited

OTHER PUBLICATIONS

R.J. Reynolds Vapor Company, IPR2018-00631, Ex. 1018: Institution Decision dated Dec. 29, 2016 (Paper 13), *Nu Mark LLC* v. *Fontem Holdings 1 B.V.*, IPR2016-01438 (P.T.A.B., petition filed Jul. 14, 2016), Mar. 2, 2018.
R.J. Reynolds Vapor Company, IPR2018-00631, Ex. 1019: Merriam-Webster's Collegiate Dictionary (11th ed. 2003) (excerpts), Mar. 2, 2018.
R.J. Reynolds Vapor Company, IPR2018-00631, Ex. 1020: U.S. Pat. No. 2,461,664 ("Smith"), Mar. 2, 2018.
R.J. Reynolds Vapor Company, IPR2018-00631, Ex. 1021: U.S. Patent No. 438,310 ("Edison"), Mar. 2, 2018.
R.J. Reynolds Vapor Company, IPR2018-00631, Ex. 1022: U.S. Pat. No. 3,200,819 ( Gilbert ), Mar. 2, 2018.
R.J. Reynolds Vapor Company, IPR2018-00631, Ex. 1023: European Patent Application Publ. EP0845220 ("Susa"), Mar. 2, 2018.
R.J. Reynolds Vapor Company, IPR2018-00631, Ex. 1024: Certified Translation of PCT International Application Publication No. WO/0028843 ("Pienemann"), Mar. 2, 2018.
R.J. Reynolds Vapor Company, IPR2018-00631, Ex. 1025: Examination Decision on the Request for Declaration of Invalidity by State Intellectual Property Office of the People's Republic of China, regarding Chinese Patent Application No. 200620090805.0 (Document 2010061800220090), Mar. 2, 2018.
R.J. Reynolds Vapor Company, IPR2018-00631, Ex. 1026: Robert W. Messier, Jr., Joining of Materials and Structures—From Pragmatic Process to Enabling Technology (2004) (excerpts), Mar. 2, 2018.
R.J. Reynolds Vapor Company, IPR2018-00631, Ex. 1027: U.S. Pat. No. 5,894,841 ("Voges"), Mar. 2, 2018.
R.J. Reynolds Vapor Company, IPR2018-00631, Ex. 1028: James A. Speck, Mechanical Fastening, Joining, and Assembly (1997) (excerpts), Mar. 2, 2018.
R.J. Reynolds Vapor Company, IPR2018-00631, Ex. 1029: U.S. Patent Application No. 2004/0234916 A1 ("Hale"), Mar. 2, 2018.
R.J. Reynolds Vapor Company, IPR2018-00631, Ex. 1030: U.S. Pat. No. 4,922,901 ("Brooks 2"), Mar. 2, 2018.
R.J. Reynolds Vapor Company, IPR2018-00631, Ex. 1031: U.S. Pat. No. 1,084,304 ("Vaughn"), Mar. 2, 2018.
R.J. Reynolds Vapor Company, IPR2018-00631, Ex. 1032: U.S. Pat. No. 3,234,357 ("Seuthe"), Mar. 2, 2018.
R.J. Reynolds Vapor Company, IPR2018-00631, Ex. 1033: U.S. Pat. No. 5,743,251 ("Howell"), Mar. 2, 2018.
R.J. Reynolds Vapor Company, IPR2018-00631, Ex. 1034: U.S. Patent Publication No. 2009/0126745 ("Hon"), Mar. 2, 2018.
R.J. Reynolds Vapor Company, IPR2018-00631, Ex. 1035: U.S. Pat. No. 5,266,746 ("Nishihara"), Mar. 2, 2018.
R.J. Reynolds Vapor Company, IPR2018-00631, Ex. 1036: European Patent No. EP1584910 ("Tohyama"), Mar. 2, 2018.
R.J. Reynolds Vapor Company, IPR2018-00631, Ex. 1037: U.S. Pat. No. 6,311,561 ("Bang"), Mar. 2, 2018.
R.J. Reynolds Vapor Company, IPR2018-00631, Ex. 1038: Photograph of Model No. MPL-502-V by Micro Pneumatic Logic (annotated image of pressure sensing port), Mar. 2, 2018.
R.J. Reynolds Vapor Company, IPR2018-00631, Ex. 1039: Photograph of Model No. MPL-502-V by Micro Pneumatic Logic (annotated image of pressure balancing port), Mar. 2, 2018.
R.J. Reynolds Vapor Company, IPR2018-00631, Ex. 1040: MPL 502 Series Specifications, Micro Pneumatic Logic, Inc., (Internet Archive webpage dated Mar. 11, 2006, https://web.archive.org/web/20060311132848/http://www.pressureswitch.com/PDFs/0502STANDARDA.pdf), Mar. 2, 2018.
R.J. Reynolds Vapor Company, IPR2018-00631, Ex. 1041: Brochure of MPL Pressure Switch Solutions, Micro Pneumatic Logic, Inc., (Internet Archive webpage dated Mar. 11, 2006, https://web.archive.org/web/20060311132419/http://www.pressureswitch.com/PDFs/2000_MPLBrochure.pdf), Mar. 2, 2018.
R.J. Reynolds Vapor Company, IPR2018-00631, Ex. 1042: U.S. Pat. No. 6,217,315 ("Mifune"), Mar. 2, 2018.
R.J. Reynolds Vapor Company, IPR2018-00631, Ex. 1043: U.S. Pat. No. 4,968,263 ("Silbernagel"), Mar. 2, 2018.
R.J. Reynolds Vapor Company, IPR2018-00631, Ex. 1044: U.S. Pat. No. 6,155,268 ("Takeuchi"), Mar. 2, 2018.
R.J. Reynolds Vapor Company, IPR2018-00631, Ex. 1045: U.S. Pat. No. 2,442,004 ("Hayward-Butt"), Mar. 2, 2018.
R.J. Reynolds Vapor Company, IPR2018-00631, Ex. 1046: U.S. Pat. No. 6,598,607 ("Adiga"), Mar. 2, 2018.
R.J. Reynolds Vapor Company, IPR2018-00631, Ex. 1047: U.S. Pat. No. 4,793,365 ("Sensabaugh"), Mar. 2, 2018.
R.J. Reynolds Vapor Company, IPR2018-00631, Ex. 1048: U.S. Pat. No. 2,472,282 ("Burchett"), Mar. 2, 2018.
R.J. Reynolds Vapor Company, IPR2018-00631, Ex. 1049: U.S. Pat. No. 2,032,695 ("Gimera"), Mar. 2, 2018.
R.J. Reynolds Vapor Company, IPR2018-00631, Ex. 1050: U.S. Pat. No. 5,745,985 ("Ghosh"), Mar. 2, 2018.
R.J. Reynolds Vapor Company, IPR2018-00631, Ex. 1051: U.S. Pat. No. 4,676,237 ("Wood"), Mar. 2, 2018.
R.J. Reynolds Vapor Company, IPR2018-00631, Ex. 1052: U.S. Pat. No. 4,945,448 ("Bremenour"), Mar. 2, 2018.
R.J. Reynolds Vapor Company, IPR2018-00631, Ex. 1053: U.S. Pat. No. 3,292,635 ("Kolodny"), Mar. 2, 2018.
R.J. Reynolds Vapor Company, IPR2018-00631, Ex. 1054: U.S. Pat. No. 3,685,521 ("Dock"), Mar. 2, 2018.
R.J. Reynolds Vapor Company, IPR2018-00631, Ex. 1055: Record of purchase of MPL-502-V-G-Range-A sensor, Mar. 2, 2018.
R.J. Reynolds Vapor Company, IPR2018-00631, Ex. 1056: Patent Owner Preliminary Response dated Oct. 29, 2015 (Paper 5), *JT International S.A.* v. *Fontem Holdings 1 B.V.*, IPR2015-01604 (P.T.A.B., petition filed Jul. 20, 2015), Mar. 2, 2018.
R.J. Reynolds Vapor Company, IPR2018-00631, Ex. 1057: Patent Owner Preliminary Response dated Oct. 20, 2015 (Paper 8), *JT International S.A.* v. *Fontem Holdings 1 B.V.*, IPR2015-01513 (P.T.A.B., petition filed Jun. 26, 2015), Mar. 2, 2018.
R.J. Reynolds Vapor Company, IPR2018-00631, Ex. 1058: PCT International Application Publication No. WO/0028843 ("Pienemann"), Mar. 2, 2018.
R.J. Reynolds Vapor Company, IPR2018-00631, Ex. 1059: Physical Sample of Model No. MPL-502-V, Range A pressure sensor by Micro Pneumatic Logic, Inc. (identified in Brooks Patent, Ex. 1003, 12:58-62) (shown in Exs. 1038-1039). Available for inspection at Petitioner's Counsel's office, Brinks Gilson & Lione., Mar. 2, 2018.
R.J. Reynolds Vapor Company, IPR2018-00631, Ex. 1060: Declaration of Kyle Yarberry, Mar. 2, 2018.
R.J. Reynolds Vapor Company, Petition for Inter Partes Review of U.S. Pat. No. 9,326,550—IPR2018-00632, Mar. 1, 2018.
R.J. Reynolds Vapor Company, IPR2018-00632, Ex. 1001: U.S. Pat. No. 9,326,550 ("The 550 Patent"), Mar. 1, 2018.
R.J. Reynolds Vapor Company, IPR2018-00632, Ex. 1002: Declaration of Dr. Robert H. Sturges regarding U.S. Pat. No. 9,326,550, Mar. 1, 2018.
R.J. Reynolds Vapor Company, IPR2018-00632, Ex. 1003: U.S. Pat. No. 3,292,635 ("Kolodny"), Mar. 1, 2018.
R.J. Reynolds Vapor Company, IPR2018-00632, Ex. 1004: U.S. Pat. No. 3,685,521 ("Dock"), Mar. 1, 2018.
R.J. Reynolds Vapor Company, IPR2018-00632, Ex. 1005: U.S. Pat. No. 5,266,746 ("Nishihara"), Mar. 1, 2018.
R.J. Reynolds Vapor Company, IPR2018-00632, Ex. 1007: Patent Owner Preliminary Response to Petition for Inter Partes Review, *Nu Mark LLC* v. *Fontem Holdings 1 B.V.*, IPR2016-01707, Paper 8 (PTAB Dec. 13, 2016) (petition filed Aug. 31, 2016), Mar. 1, 2018.
R.J. Reynolds Vapor Company, IPR2018-00632, Ex. 1008: Termination Order, *Nu Mark LLC* v. *Fontem Holdings 1 B.V.*, IPR2016-01706, Paper 12 (PTAB Jan. 4, 2017) (petition filed Aug. 31, 2016) (Order issued in multiple IPRs—caption is IPR2016-01288).
R.J. Reynolds Vapor Company, IPR2018-00632, Ex. 1009: Decision Denying Institution of Inter Partes Review, *Nu Mark LLC* v. *Fontem Holdings 1 B.V.*, IPR2016-01283, Paper 12 (PTAB Nov. 30, 2016) ( petition filed Jun. 28, 2016), Mar. 1, 2018.
R.J. Reynolds Vapor Company, IPR2018-00632, Ex. 1010: Decision Denying Institution of Inter Partes Review, *Nu Mark LLC* v. *Fontem Holdings 1 B.V.*, IPR2016-01438, Paper 13 (PTAB Dec. 29, 2016) (PTAB, petition filed Jul. 14, 2016), Mar. 1, 2018.

(56) References Cited

OTHER PUBLICATIONS

R.J. Reynolds Vapor Company, IPR2018-00632, Ex. 1011: The Oxford American Dictionary and Thesaurus with Language Guide, Oxford University Press 2003—Excerpt, Mar. 1, 2018.
R.J. Reynolds Vapor Company, IPR2018-00632, Ex. 1012: Random House Webster's Unabridged Dictionary, Second Edition, Random House, 2001—Excerpt, Mar. 1, 2018.
R.J. Reynolds Vapor Company, IPR2018-00632, Ex. 1013: Decision Denying Institution of Inter Partes Review, *R.J. Reynolds Vapor Company* v. *Fontem Holdings 1 B.V.*, IPR2016-01859, Paper 8 (PTAB Mar. 13, 2017) (petition filed Sep. 23, 2016), Mar. 1, 2018.
R.J. Reynolds Vapor Company, IPR2018-00632, Ex. 1014: U.S. Pat. No. 4,968,263 ("Silbernagel"), Mar. 1, 2018.
R.J. Reynolds Vapor Company, IPR2018-00632, Ex. 1015: U.S. Pat. No. 6,311,561 ("Bang"), Mar. 1, 2018.
R.J. Reynolds Vapor Company, IPR2018-00632, Ex. 1016: U.S. Pat. No. 2,057,353 ("Whittemore"), Mar. 1, 2018.
R.J. Reynolds Vapor Company, IPR2018-00632, Ex. 1017: U.S. Pat. No. 4,947,874 ("Brooks"), Mar. 1, 2018.
R.J. Reynolds Vapor Company, IPR2018-00632, Ex. 1018: U.S. Pat. No. 5,894,841 ("Voges"), Mar. 1, 2018.
R.J. Reynolds Vapor Company, IPR2018-00632, Ex. 1019: U.S. Pat. No. 6,155,268 ("Takeuchi"), Mar. 1, 2018.
R.J. Reynolds Vapor Company, IPR2018-00632, Ex. 1020: U.S. Pat. No. 2,442,004 ("Hayward-Butt"), Mar. 1, 2018.
R.J. Reynolds Vapor Company, IPR2018-00632, Ex. 1021: U.S. Pat. No. 3,200,819 ("Gilbert"), Mar. 1, 2018.
R.J. Reynolds Vapor Company, IPR2018-00632, Ex. 1022: U.S. Pat. No. 6,598,607 ("Adiga"), Mar. 1, 2018.
R.J. Reynolds Vapor Company, IPR2018-00632, Ex. 1023: U.S. Pat. No. 4,793,365 ("Sensabaugh"), Mar. 1, 2018.
R.J. Reynolds Vapor Company, IPR2018-00632, Ex. 1024: U.S. Pat. No. 5,203,355 ("Clearman"), Mar. 1, 2018.
R.J. Reynolds Vapor Company, IPR2018-00632, Ex. 1025: U.S. Pat. No. 2,472,282 ("Burchett"), Mar. 1, 2018.
R.J. Reynolds Vapor Company, IPR2018-00632, Ex. 1026: U.S. Pat. No. 2,032,695 ("Gimera"), Mar. 1, 2018.
R.J. Reynolds Vapor Company, IPR2018-00632, Ex. 1027: U.S. Pat. No. 5,743,251 ("Howell"), Mar. 1, 2018.
R.J. Reynolds Vapor Company, IPR2018-00632, Ex. 1028: European Patent Application EP 0 845 220 A1 ("Susa"), Mar. 1, 2018.
R.J. Reynolds Vapor Company, IPR2018-00632, Ex. 1029: U.S. Pat. No. 2,461,664 ("Smith"), Mar. 1, 2018.
R.J. Reynolds Vapor Company, IPR2018-00632, Ex. 1030: U.S. Pat. No. 3,234,357 ("Seuthe"), Mar. 1, 2018.
R.J. Reynolds Vapor Company, IPR2018-00632, Ex. 1031: U.S. Pat. No. 5,745,985 ("Ghosh"), Mar. 1, 2018.
R.J. Reynolds Vapor Company, IPR2018-00632, Ex. 1032: U.S. Pat. No. 4,676,237 ("Wood"), Mar. 1, 2018.
R.J. Reynolds Vapor Company, IPR2018-00632, Ex. 1033: U.S. Pat. No. 4,945,448 ("Bremenour"), Mar. 1, 2018.
R.J. Reynolds Vapor Company, IPR2018-00632, Ex. 1034: Robert W. Messier, Jr., Joining of Materials and Structures, Elsevier Butterworth-Heinemann 2004—Excerpt, Mar. 1, 2018.
R.J. Reynolds Vapor Company, IPR2018-00632, Ex. 1035: U.S. Pat. No. 438,310 ("Edison"), Mar. 1, 2018.
R.J. Reynolds Vapor Company, IPR2018-00632, Ex. 1036: PCT International Application Publication No. WO/28843 (Pienemann), Mar. 1, 2018.
R.J. Reynolds Vapor Company, IPR2018-00632, Ex. 1037: Certified Translation of PCT International Application Publication No. WO/28843 (Pienemann), Mar. 1, 2018.
R.J. Reynolds Vapor Company, IPR2018-00632, Ex. 1038: U.S. Pat. No. 5,177,424 ("Connors"), Mar. 1, 2018.
R.J. Reynolds Vapor Company, IPR2018-00632, Ex. 1039: European Patent No. 1584910 ("Tohyama"), Mar. 1, 2018.
R.J. Reynolds Vapor Company, IPR2018-00632, Ex. 1040: U.S. Pat. No. 1,517,584 ("Reece"), Mar. 1, 2018.
R.J. Reynolds Vapor Company, IPR2018-00632, Ex. 1041: U.S. Pat. No. 780,087 ("Burt"), Mar. 1, 2018.
R.J. Reynolds Vapor Company, IPR2018-00632, Ex. 1042: U.S. Pat. No. 2,959,664 ("Fenn"), Mar. 1, 2018.
R.J. Reynolds Vapor Company, IPR2018-00632, Ex. 1043: Examination Decision on the Request for Declaration of Invalidity dated Jun. 23, 2010, 5W11580, State Intellectual Property Office of the People's Republic of China, with English translation, Mar. 1, 2018.
R.J. Reynolds Vapor Company, IPR2018-00632, Ex. 1044: James A. Speck, Mechanical Fastening, Joining, and Assembly, Marcel Dekker, Inc. 1997, Mar. 1, 2018.
R.J. Reynolds Vapor Company, IPR2018-00632, Ex. 1045: Patent Owner Preliminary Response to Petition for Inter Partes Review, *JT International S.A.* v. *Fontem Holdings 1 B.V.*, IPR2015-01604, Paper 5 (PTAB Oct. 29, 2015) (petition filed Jul. 20, 2015), Mar. 1, 2018.
R.J. Reynolds Vapor Company, IPR2018-00632, Ex. 1046: Patent Owner Preliminary Response to Petition for Inter Partes Review, *JT International S.A.* v. *Fontem Holdings 1 B.V.*, IPR2015-01513, Paper 8 (PTAB Oct. 20, 2015) (petition filed Jun. 26, 2015), Mar. 1, 2018.
R.J. Reynolds Vapor Company, IPR2018-00632, Ex. 1047: U.S. Appl. No. 2004/0234916 A1 ("Hale"), Mar. 1, 2018.
R.J. Reynolds Vapor Company, IPR2018-00632, Ex. 1048: U.S. Pat. No. 4,922,901 ("Brooks 2"), Mar. 1, 2018.
R.J. Reynolds Vapor Company, IPR2018-00632, Ex. 1049: U.S. Pat. No. 1,084,304 ("Vaughn"), Mar. 1, 2018.
R.J. Reynolds Vapor Company, IPR2018-00632, Ex. 1050: Model No. MPL-502-V by Micro Pneumatic Logic, annotated image of pressure sensing port, Mar. 1, 2018.
R.J. Reynolds Vapor Company, IPR2018-00632, Ex. 1051: Model No. MPL-502-V by Micro Pneumatic Logic, annotated image of pressure balancing port, Mar. 1, 2018.
R.J. Reynolds Vapor Company, IPR2018-00632, Ex. 1052: MPL Pressure Switch Solutions, Micro Pneumatic Logic, Inc., (Mar. 11, 2006), http://www.pressureswitch.com/PDFs/2000_MPLBrochure.pdf [https://web.archive.org/web/20060311132419/http://www.pressureswitch.com/PDFs/2000_MPLBrochure.pdf], Mar. 1, 2018.
R.J. Reynolds Vapor Company, IPR2018-00632, Ex. 1053: U.S. Pat. No. 2,086,192 ("Schumaker"), Mar. 1, 2018.
R.J. Reynolds Vapor Company, IPR2018-00632, Ex. 1054: Denying Institution of Inter Partes Review, *Nu Mark LLC.* v. *Fontem Holdings 1 B.V.*, IPR2016-01307, Paper 12 (PTAB Dec. 23, 2016) (petition filed Jun. 28, 2016), Mar. 1, 2018.
R.J. Reynolds Vapor Company, IPR2018-00632, Ex. 1056: MPL 502 Series Specifications, Micro Pneumatic Logic, Inc., (Mar. 11, 2006), http://www.pressureswitch.com/PDFs/0502STANDARDA.pdf [https://web.archive.org/web/20060311132848/http://www.pressureswitch.com/PDFs/0502STANDARDA.pdf], Mar. 1, 2018.
R.J. Reynolds Vapor Company, IPR2018-00632, Ex. 1057: Record of purchase of MPL-502-V-G-Range-A sensor, Mar. 1, 2018.
R.J. Reynolds Vapor Company, IPR2018-00632, Ex. 1059: Physical Sample of Model No. MPL-502-V, Range A pressure sensor by Micro Pneumatic Logic, Inc. (identified in Brooks Patent, Ex. 1017, 12:58-62) (shown in Exs. 1050, 1051). Available for inspection at Petitioner's Counsel's office, Brinks Gilson & Lione., Mar. 1, 2018.
R.J. Reynolds Vapor Company, IPR2018-00632, Ex. 1060: Declaration of Kyle Yarberry, Mar. 1, 2018.
R.J. Reynolds Vapor Company, IPR2018-00632, Ex. 1061: Merriam-Webster's Collegiate Dictionary (11th ed. 2003)—Excerpt, Mar. 1, 2018.
R.J. Reynolds Vapor Company, IPR2018-00632, Ex. 1062: Excerpt from File History for U.S. Pat. No. 9,326,550 (U.S. Appl. No. 14/720,288): Information Disclosure Statements initiated by Examiner (dated Jan. 20, 2016), Mar. 1, 2018.
R.J. Reynolds Vapor Company, Petition for Inter Partes Review of U.S. Pat. No. 9,326,551—IPR2018-00633, Mar. 1, 2018.
R.J. Reynolds Vapor Company, IPR2018-00633, Ex. 1001: U.S. Pat. No. 9,326,551 ("the 551 Patent"), Mar. 1, 2018.
R.J. Reynolds Vapor Company, IPR2018-00633, Ex. 1002: Declaration of Dr. Robert H. Sturges regarding U.S. Pat. No. 9,326,551, Mar. 1, 2018.
R.J. Reynolds Vapor Company, IPR2018-00633, Ex. 1003: Excerpt from File History for U.S. Pat. No. 9,326,551 (U.S. Appl. No.

(56) References Cited

OTHER PUBLICATIONS

14/723,209): Information Disclosure Statements initiated by Examiner (dated Jan. 15, 2016), Mar. 1, 2018.
R.J. Reynolds Vapor Company, IPR2018-00633, Ex. 1007: Patent Owner Preliminary Response to Petition for Inter Partes Review, *Nu Mark LLC* v. *Fontem Holdings 1 B.V.*, IPR2016-01706, Paper 9 (PTAB Dec. 12, 2016) (petition filed Aug. 31, 2016), Mar. 1, 2018.
R.J. Reynolds Vapor Company, IPR2018-00633, Ex. 1008: Termination Order, *Nu Mark LLC* v. *Fontem Holdings 1 B.V.*, IPR2016-01706, Paper 12 (PTAB Jan. 4, 2017) (petition filed Aug. 31, 2016) (Order issued in multiple IPRs—caption is IPR2016-01288), Mar. 1, 2018.
R.J. Reynolds Vapor Company, IPR2018-00633, Ex. 1009: Decision Denying Institution of Inter Partes Review, *Nu Mark LLC* v. *Fontem Holdings 1 B.V.*, IPR2016-01283, Paper 12 (PTAB Nov. 30, 2016) (petition filed Jun. 28, 2016), Mar. 1, 2018.
R.J. Reynolds Vapor Company, IPR2018-00633, Ex. 1010: Decision Denying Institution of Inter Partes Review, *Nu Mark LLC* v. *Fontem Holdings 1 B.V.*, IPR2016-01438, Paper 13 (PTAB Dec. 29, 2016) (petition filed Jul. 14, 2016), Mar. 1, 2018.
R.J. Reynolds Vapor Company, IPR2018-00633, Ex. 1011: The Oxford American Dictionary and Thesaurus with Language Guide, Oxford University Press 2003—Excerpt, Mar. 1, 2018.
R.J. Reynolds Vapor Company, IPR2018-00633, Ex. 1012: Random House Webster's Unabridged Dictionary, Second Edition, Random House, 2001—Excerpt, Mar. 1, 2018.
R.J. Reynolds Vapor Company, IPR2018-00633, Ex. 1013: Decision Denying Institution of Inter Partes Review, *R.J. Reynolds Vapor Company* v. *Fontem Holdings 1 B.V.*, IPR2016-01859, Paper 8 (PTAB Mar. 13, 2017) (petition filed Sep. 23, 2016), Mar. 1, 2018.
R.J. Reynolds Vapor Company, IPR2018-00633, Ex. 1014: McGraw-Hill Dictionary of Scientific and Technical Terms, Fifth Edition, McGraw-Hill, Inc. 1994—Excerpt, Mar. 1, 2018.
R.J. Reynolds Vapor Company, IPR2018-00633, Ex. 1015: Webster's Third New International Dictionary of the English Language Unabridged, Merriam-Webster Inc. 1993—Excerpt, Mar. 1, 2018.
R.J. Reynolds Vapor Company, IPR2018-00633, Ex. 1016: U.S. Pat. No. 2,057,353 ("Whittemore"), Mar. 1, 2018.
R.J. Reynolds Vapor Company, IPR2018-00633, Ex. 1017: U.S. Pat. No. 4,947,874 ("Brooks"), Mar. 1, 2018.
R.J. Reynolds Vapor Company, IPR2018-00633, Ex. 1018: U.S. Pat. No. 5,894,841 ("Voges"), Mar. 1, 2018.
R.J. Reynolds Vapor Company, IPR2018-00633, Ex. 1019: U.S. Pat. No. 6,155,268 ("Takeuchi"), Mar. 1, 2018.
R.J. Reynolds Vapor Company, IPR2018-00633, Ex. 1020: U.S. Pat. No. 2,442,004 ("Hayward-Butt"), Mar. 1, 2018.
R.J. Reynolds Vapor Company, IPR2018-00633, Ex. 1021: U.S. Pat. No. 3,200,819 ("Gilbert"), Mar. 1, 2018.
R.J. Reynolds Vapor Company, IPR2018-00633, Ex. 1022: U.S. Pat. No. 6,598,607 ("Adiga"), Mar. 1, 2018.
R.J. Reynolds Vapor Company, IPR2018-00633, Ex. 1023: U.S. Pat. No. 4,793,365 ("Sensabaugh"), Mar. 1, 2018.
R.J. Reynolds Vapor Company, IPR2018-00633, Ex. 1024: U.S. Pat. No. 5,203,355 ("Clearman"), Mar. 1, 2018.
R.J. Reynolds Vapor Company, IPR2018-00633, Ex. 1025: U.S. Pat. No. 2,472,282 ("Burchett"), Mar. 1, 2018.
R.J. Reynolds Vapor Company, IPR2018-00633, Ex. 1026: U.S. Pat. No. 2,032,695 ("Gimera"), Mar. 1, 2018.
R.J. Reynolds Vapor Company, IPR2018-00633, Ex. 1027: U.S. Pat. No. 5,743,251 ("Howell"), Mar. 1, 2018.
R.J. Reynolds Vapor Company, IPR2018-00633, Ex. 1028: European Patent Application EP 0 845 220 A1 ("Susa"), Mar. 1, 2018.
R.J. Reynolds Vapor Company, IPR2018-00633, Ex. 1029: U.S. Pat. No. 2,461,664 ("Smith"), Mar. 1, 2018.
R.J. Reynolds Vapor Company, IPR2018-00633, Ex. 1030: U.S. Pat. No. 3,234,357 ("Seuthe"), Mar. 1, 2018.
R.J. Reynolds Vapor Company, IPR2018-00633, Ex. 1031: U.S. Pat. No. 5,745,985 ("Ghosh"), Mar. 1, 2018.
R.J. Reynolds Vapor Company, IPR2018-00633, Ex. 1032: U.S. Pat. No. 4,676,237 ("Wood"), Mar. 1, 2018.
R.J. Reynolds Vapor Company, IPR2018-00633, Ex. 1033: U.S. Pat. No. 4,945,448 ("Bremenour"), Mar. 1, 2018.
R.J. Reynolds Vapor Company, IPR2018-00633, Ex. 1034: Robert W. Messier, Jr., Joining of Materials and Structures, Elsevier Butterworth-Heinemann 2004—Excerpt, Mar. 1, 2018.
R.J. Reynolds Vapor Company, IPR2018-00633, Ex. 1035: U.S. Pat. No. 438,310 ("Edison"), Mar. 1, 2018.
R.J. Reynolds Vapor Company, IPR2018-00633, Ex. 1036: PCT International Application Publication No. WO/28843 ("Pienemann"), Mar. 1, 2018.
R.J. Reynolds Vapor Company, IPR2018-00633, Ex. 1037: Certified Translation of PCT International Application Publication No. WO/28843 ("Pienemann"), Mar. 1, 2018.
R.J. Reynolds Vapor Company, IPR2018-00633, Ex. 1038: U.S. Pat. No. 5,177,424 ("Connors"), Mar. 1, 2018.
R.J. Reynolds Vapor Company, IPR2018-00633, Ex. 1039: Merriam-Webster's Collegiate Dictionary (11th ed. 2003)—Excerpt, Mar. 1, 2018.
R.J. Reynolds Vapor Company, IPR2018-00633, Ex. 1040: U.S. Pat. No. 1,517,584 ("Reece"), Mar. 1, 2018.
R.J. Reynolds Vapor Company, IPR2018-00633, Ex. 1041: U.S. Pat. No. 780,087 ("Burt"), Mar. 1, 2018.
R.J. Reynolds Vapor Company, IPR2018-00633, Ex. 1042: U.S. Pat. No. 2,959,664 ("Fenn"), Mar. 1, 2018.
R.J. Reynolds Vapor Company, IPR2018-00633, Ex. 1043: Examination Decision on the Request for Declaration of Invalidity dated Jun. 23, 2010, 5W11580, State Intellectual Property Office of the People's Republic of China, with English translation, Mar. 1, 2018.
R.J. Reynolds Vapor Company, IPR2018-00633, Ex. 1044: James A. Speck, Mechanical Fastening, Joining, and Assembly, Marcel Dekker, Inc. 1997, Mar. 1, 2018.
R.J. Reynolds Vapor Company, IPR2018-00633, Ex. 1045: Patent Owner Preliminary Response to Petition for Inter Partes Review, *JT International S.A.* v. *Fontem Holdings 1 B.V.*, IPR2015-01604, Paper 5 (PTAB Oct. 29, 2015) (petition filed Jul. 20, 2015), Mar. 1, 2018.
R.J. Reynolds Vapor Company, IPR2018-00633, Ex. 1046: Patent Owner Preliminary Response to Petition for Inter Partes Review, *JT International S.A.* v. *Fontem Holdings 1 B.V.*, IPR2015-01513, Paper 8 (PTAB Oct. 20, 2015) (petition filed Jun. 26, 2015), Mar. 1, 2018.
R.J. Reynolds Vapor Company, IPR2018-00633, Ex. 1047: U.S. Patent Application No. 2004/0234916 A1 ("Hale"), Mar. 1, 2018.
R.J. Reynolds Vapor Company, IPR2018-00633, Ex. 1048: U.S. Pat. No. 4,922,901 ("Brooks 2"), Mar. 1, 2018.
R.J. Reynolds Vapor Company, IPR2018-00633, Ex. 1049: U.S. Pat. No. 1,084,304 ("Vaughn"), Mar. 1, 2018.
R.J. Reynolds Vapor Company, IPR2018-00633, Ex. 1051: U.S. Pat. No. 4,920,990 ("Lawrence"), Mar. 1, 2018.
R.J. Reynolds Vapor Company, IPR2018-00633, Ex. 1052: U.S. Pat. No. 5,005,593 ("Fagg"), Mar. 1, 2018.
R.J. Reynolds Vapor Company, IPR2018-00633, Ex. 1053: U.S. Pat. No. 2,086,192 ("Schumaker"), Mar. 1, 2018.
R.J. Reynolds Vapor Company, IPR2018-00633, Ex. 1054: Decision Denying Institution of Inter Partes Review, *Nu Mark LLC.* v. *Fontem Holdings 1 B.V.*, IPR2016-01307, Paper 12 (PTAB Dec. 23, 2016) (petition filed Jun. 28, 2016), Mar. 1, 2018.
R.J. Reynolds Vapor Company, IPR2018-00633, Ex. 1055: U.S. Pat. No. 4,506,682 ("Muller"), Mar. 1, 2018.
R.J. Reynolds Vapor Company, IPR2018-00633, Ex. 1056: Declaration of Kyle Yarberry, Mar. 1, 2018.
R.J. Reynolds Vapor Company, Answer to Complaint in *Fontem Ventures B.V.* v. *R.J. Reynolds Vapor Company*, 16-CV-4534, Dkt. 022, Jul. 25, 2017.
R.J. Reynolds Vapor Company, Preliminary Invalidity Contentions in *Fontem Ventures B.V.* v. *R.J. Reynolds Vapor Company*, 16-cv-01255, Mar. 15, 2017.
R.J. Reynolds Vapor Company, Preliminary Invalidity Contentions, Exhibit G ('205 patent), 16-cv-01255, Mar. 15, 2017.
R.J. Reynolds Vapor Company, Preliminary Invalidity Contentions *Fontem Ventures B.V.* v. *R.J. Reynolds Vapor Company*, 17-cv-0175, Jul. 31, 2017.

(56) References Cited

OTHER PUBLICATIONS

R.J. Reynolds Vapor Company, Preliminary Invalidity Contentions, Exhibit A (U.S. Pat. No. 8,375,957), 17-cv-0175, Jul. 31, 2017.
R.J. Reynolds Vapor Company, Preliminary Invalidity Contentions, Exhibit B (U.S. Pat. No. 8,863,752 patent), 17-cv-0175, Jul. 31, 2017.
R.J. Reynolds Vapor Company, Preliminary Invalidity Contentions, Exhibit C (U.S. Pat. No. 9,326,550 patent), 17-cv-0175, Jul. 31, 2017.
R.J. Reynolds Vapor Company, Preliminary Invalidity Contentions, Exhibit D (U.S. Pat. No. 9,326,551 patent), 17-cv-0175, Jul. 31, 2017.
R.J. Reynolds Vapor Company, Preliminary Invalidity Contentions, Exhibit E (U.S. Pat. No. 9,339,062 patent), 17-cv-0175, Jul. 31, 2017.
R.J. Reynolds Vapor Company, *Fontem Holdings B.V.* v. *R.J. Reynolds Vapor Company,* U.S. District Court, Middle District of North Carolina, Case 16-cv-1255 and consolidated cases, Final Invalidity Contentions(relating to U.S. Pat. No. 8,365,742, U.S. Pat. No. 8,490,628, U.S. Pat. No. 8,893,726, U.S. Pat. No. 8,899,239, U.S. Pat. No. 8,326,548, U.S. Pat. No. 8,326,549, and U.S. Pat. No. 9,370,205), May 7, 2018.
R.J. Reynolds Vapor Company, *Fontem Holdings B.V.* v. *R.J. Reynolds Vapor Company,* U.S. District Court, Middle District of North Carolina, Case 16-cv-1255 and consolidated cases, Final Invalidity Elections (relating to U.S. Pat. No. 8,365,742, U.S. Pat. No. 8,490,628, U.S. Pat. No. 8,893,726, U.S. Pat. No. 8,899,239, U.S. Pat. No. 8,326,548, U.S. Pat. No. 8,326,549, and U.S. Pat. No. 9,370,205), May 7, 2018.
R.J. Reynolds Vapor Company, 16-cv-1255 and consolidated cases, Final Invalidity Contentions, Amended Exhibit G (U.S. Pat. No. 9,370,205), May 7, 2018.
R.J. Reynolds Vapor Company, *Fontem Holdings B.V.* v. *R.J. Reynolds Vapor Company,* U.S. District Court, Middle District of North Carolina, Case 16-cv-1255 and consolidated cases, Final Invalidity Elections (relating to U.S. Pat. No. 8,375,957, U.S. Pat. No. 8,863,752 U.S. Pat. No. 9,326,550, U.S. Pat. No. 9,326,551, U.S. Pat. No. 9,339,062, U.S. Pat. No. 8,393,331, U.S. Pat. No. 9,364,027, and U.S. Pat. No. 9,456,632), May 7, 2018.
R.J. Reynolds Vapor Company, *Fontem Holdings B.V.* v. *R.J. Reynolds Vapor Company,* U.S. District Court, Middle District of North Carolina, Case 16-cv-1255 and consolidated cases, Final Invalidity Contentions (relating to U.S. Pat. No. 8,375,957, U.S. Pat. No. 8,863,752 U.S. Pat. No. 9,326,550, U.S. Pat. No. 9,326,551, U.S. Pat. No. 9,339,062, U.S. Pat. No. 8,393,331, U.S. Pat. No. 9,364,027, and U.S. Pat. No. 9,456,632), May 7, 2018.
R.J. Reynolds Vapor Company, 16-cv-1255 and consolidated cases, Final Invalidity Contentions, Amended Exhibit A (U.S. Pat. No. 8,375,957), May 7, 2018.
R.J. Reynolds Vapor Company, 16-cv-1255 and consolidated cases, Final Invalidity Contentions, Amended Exhibit B (U.S. Pat. No. 8,863,752), May 7, 2018.
R.J. Reynolds Vapor Company, 16-cv-1255 and consolidated cases, Final Invalidity Contentions, Amended Exhibit C (U.S. Pat. No. 9,326,550), May 7, 2018.
R.J. Reynolds Vapor Company, 16-cv-1255 and consolidated cases, Final Invalidity Contentions, Amended Exhibit D (U.S. Pat. No. 9,326,551), May 7, 2018.
R.J. Reynolds Vapor Company, 16-cv-1255 and consolidated cases, Final Invalidity Contentions, Amended Exhibit E (U.S. Pat. No. 9,339,062), May 7, 2018.
State Intellectual Property Office China PRC, Decision of Patent Invalidation Petition, Mar. 3, 2014.
State Intellectual Property Office China PRC, Examination Decision on the Invalidity Declaration Application for CNZL200620090805.0, Jun. 23, 2010.
State Intellectual Property Office PRC China, English translation of Written Opinion for PCT/CN07/001576, dated Aug. 16, 2007.
State Intellectual Property Office PRC China, International Search Report for PCT/CN07/001576, dated Aug. 16, 2007.
State Intellectual Property Office PRC China, Search Report for Utility Model CNZL200620090805.0, dated Nov. 18, 2008.
Techpowerup Internet Webpage, http://www.techpowerup.com/articles/overclocking/voltmods/21, May 24, 2004.
U.S. District Court for the Central District of California, *Fontem Ventures B.V.* v. *NJOY, Inc.,* Case 2:14-cv-01645-GW-MRW, Dkt. No. 65, Rulings on Claims Construction, Jan. 29, 2015, 28 pgs.
U.S. District Court, Central District of California, *Fontem Ventures B.V., et al.* v. *NJOY, Inc., et al.,* Case No. CV 14-1645-GW (MRWx), Dkt. No. 133, Markman Hearing/Claim Construction Final Ruling, May 7, 2015, 16 pgs.
U.S. District Court, Middle District of North Carolina, *Fontem Ventures B.V., et al.* v. *NJOY, Inc., et al.,* Case No. 16-cv-01255, Dkt. No. 148, Claim Construction Order, Mar. 12, 2018, 8 pgs.
U.S. Appl. No. 12/226,819, Non-Final Office Action, dated Oct. 5, 2010.
U.S. Appl. No. 12/226,819, Final Office Action, dated Jun. 8, 2011.
U.S. Appl. No. 12/226,819, Non-Final Office Action, dated Jan. 9, 2012.
U.S. Appl. No. 12/226,819, Non-Final Office Action, dated Aug. 7, 2012.
U.S. Appl. No. 12/226,819, Notice of Allowance, dated Dec. 17, 2012.
U.S. Appl. No. 13/754,521, Non-Final Office Action, dated Sep. 25, 2015.
U.S. Appl. No. 13/754,521, Notice of Allowance, dated Apr. 20, 2016.
U.S. Appl. No. 13/915,427, Non-Final Office Action, dated Mar. 21, 2014.
U.S. Appl. No. 13/915,427, Notice of Allowance, dated Aug. 19, 2014.
U.S. Appl. No. 14/720,288, Notice of Allowance, dated Jan. 20, 2016.
U.S. Appl. No. 14/723,209, Notice of Allowance, dated Jan. 15, 2016.
U.S. Appl. No. 14/723,244, Notice of Allowance, dated Jan. 20, 2016.
U.S. Appl. No. 15/158,421, Non-Final Office Action, dated Aug. 18, 2016.
U.S. Appl. No. 15/158,421, Final Office Action, dated Jan. 17, 2017.
U.S. Appl. No. 15/158,421, Notice of Allowance, dated Aug. 10, 2017.
U.S. Appl. No. 15/158,421, Corrected Notice of Allowance, dated Sep. 29, 2017.
U.S. Appl. No. 15/634,698, Non-Final Office Action, dated Oct. 4, 2017.
U.S. Appl. No. 15/634,698, Non-Final Office Action, dated May 3, 2018.
U.S. Appl. No. 15/634,698, Notice of Allowance, dated Oct. 3, 2018.
CN2719043 (Machine Translation) [online], [retrieved on Aug. 30, 2018], retrieved from Espacenet(https://u worldwide .espacenet.com/publicationDetails/description?CC=CN &NR=2719043Y&KC=Y&FT= D&N D=&date=20050824&D B=&locale=) (Year: 2005) (cited in U.S. Appl. No. 15/634,698 Notice of Allowance).

* cited by examiner

ELECTRONIC CIGARETTE

CROSS-REFERENCE TO RELATED APPLICATIONS

This application is a continuation of U.S. application Ser. No. 15/634,698, filed Jun. 27, 2017 and now pending, which is a continuation of U.S. patent application Ser. No. 15/158,421, filed May 18, 2016, now U.S. Pat. No. 9,808,033, which is a continuation of U.S. patent application Ser. No. 13/754,521, filed Jan. 30, 2013, now U.S. Pat. No. 9,370,205, which is a continuation of U.S. patent application Ser. No. 12/226,819, filed Jan. 15, 2009, now U.S. Pat. No. 8,375,957, which is a § 371 national phase application of International Patent Application No. PCT/CN2007/001576, filed May 15, 2007, which claims the benefit of Chinese Patent Application No. 200620090805.0, filed May 16, 2006. All of these applications are incorporated herein by reference in their entirety.

BACKGROUND

Although smoking causes serious respiratory diseases and cancers, it is difficult to get smokers to quit smoking. Nicotine is the effective ingredient in cigarettes. Nicotine is a micro-molecular alkaloid which is basically harmless to humans at low dosages. Tar is the major harmful substance in tobacco. Tobacco tar contains thousands of ingredients, dozens of which are carcinogenic.

Cigarette substitutes have used relatively pure nicotine in patches, chewing gum and aerosols. Still disadvantages remain with cigarette substitutes or products for helping smokers to quit smoking.

SUMMARY OF THE INVENTION

An improved electronic cigarette has a battery assembly, an atomizer assembly and a cigarette bottle assembly. The battery assembly connects with one end of the atomizer assembly, and the cigarette bottle assembly is inserted into the other end of the atomizer assembly, thus forming one cigarette type or cigar type body. Use of the electronic cigarette reduces cancer risks and fire hazards while providing a simulated smoking experience.

DETAILED DESCRIPTION OF THE DRAWINGS

Figure 1:
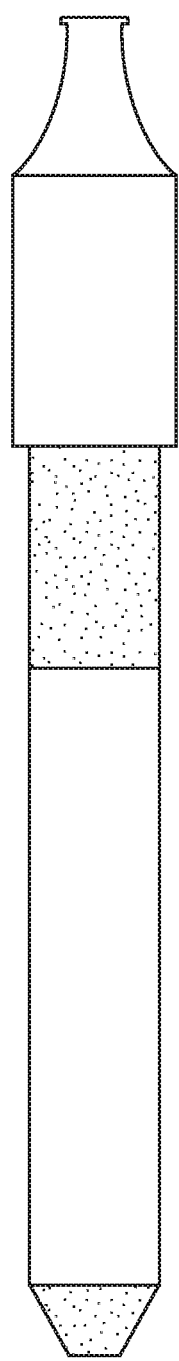
FIG. 1 is a side view of an electronic cigarette.
Figure 2A:
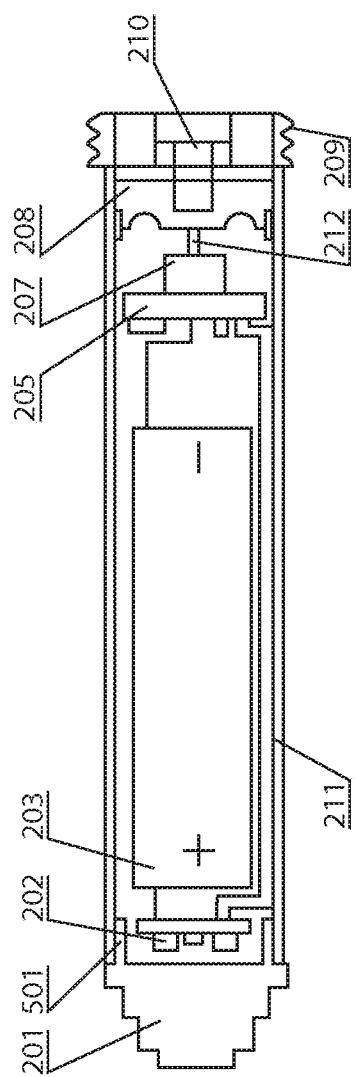
FIG. 2A is a view of the battery assembly.

As shown in FIG. 1, an electronic cigarette has an appearance similar to a cigarette inserted into the cigarette holder. As shown in FIG. 2A, the electronic cigarette includes a battery assembly, an atomizer assembly and a cigarette bottle assembly. An external thread electrode (209) is located in one end of the battery assembly, and an internal thread electrode (302) is located in one end of the atomizer assembly. The battery assembly and atomizer assembly are connected through the screw thread electrode into an electronic cigarette. The cigarette bottle assembly is inserted into the other end of atomizer assembly.

As shown in FIG. 2A, the battery assembly includes an indicator (202), lithium ion battery (203), MOSFET electric circuit board (205), sensor (207), silica gel corrugated membrane (208), primary screw thread electrode (209), primary negative pressure cavity (210), and primary shell (211). On one end of the primary shell (211) is an external thread electrode (209). On the other end is an indicator (202), where there is an indicator cap (201) on one side having a small hole (501). On the other side, the lithium ion battery (203) and MOSFET (Metallic Oxide Semiconductor Field Effect Tube) electric circuit board (205) are connected successively. The sensor (207) is located on MOSFET electric circuit board (205). Between the primary screw thread electrode (209) and sensor (207) is a silica gel corrugated membrane (208), on which there is the primary negative pressure cavity (210). The sensor (207) is connected with the silica gel corrugated membrane (208) through the switch spring (212).

The sensor (207) may be switch sensor made of elastic alloy slice, a linear output Hall sensor, a semiconductor force-sensitive chip, a semiconductor matrix thermoelectric bridge chip, capacitance or inductance sensor. The indicators (202) include two red LEDs. The lithium ion battery (203) may be either a rechargeable polymer lithium ion battery or a rechargeable lithium ion battery. The external thread electrode (209) is a gold-coated stainless steel or brass part with a hole drilled in the center. The silica gel corrugated membrane (208) may alternatively be made of fluorinated rubber, butyronitrile rubber, or elastic alloy film.

Figure 3:
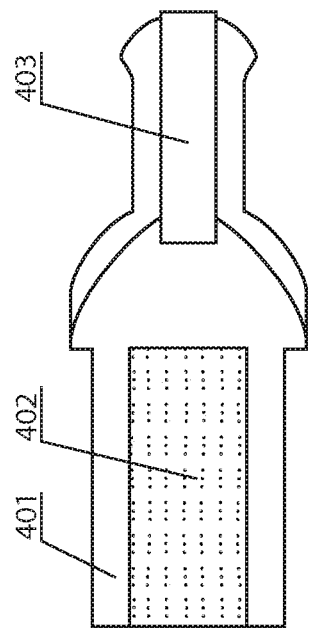
FIG. 3 is the diagram of the atomizer assembly.

As shown in FIG. 3, the atomizer assembly includes the internal thread electrode (302), air-liquid separator (303), atomizer (307) and the secondary shell (306). One end of the secondary shell (306) is inserted into the cigarette bottle assembly for connection, while the other end has an internal thread electrode (302), in which there is the secondary negative pressure cavity (301). The air-liquid separator (303) and the atomizer (307) are connected with the internal thread electrode (302) successively. On the secondary shell (306), there is an air intake hole (502). The air-liquid separator (303) is made of stainless steel or plastic with a hole. The internal thread electrode (302) is a gold-coated stainless steel or brass part with a hole in the center.

Figure 4:
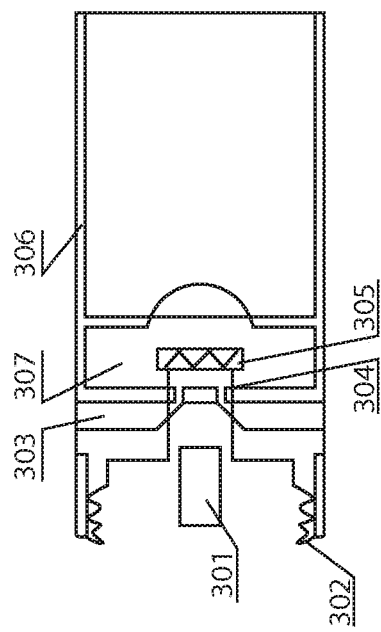
FIG. 4 is the diagram of the cigarette bottle assembly.
Figure 8:
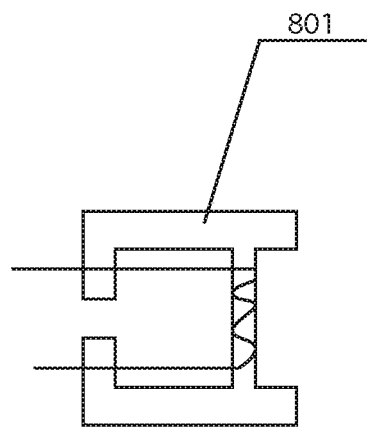
FIG. 8 is a side view of an atomizer.
Figure 9:
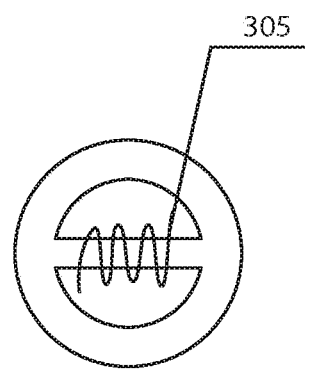
FIG. 9 is an end view of the atomizer shown in FIG. 8.
Figure 10:
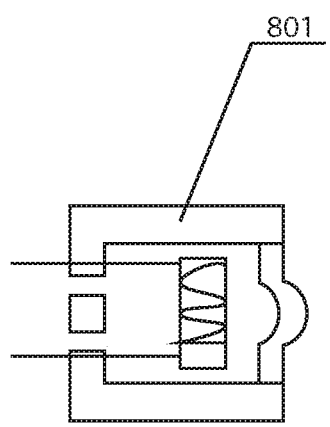
FIG. 10 is a diagram of a spray atomizer.
Figure 11:
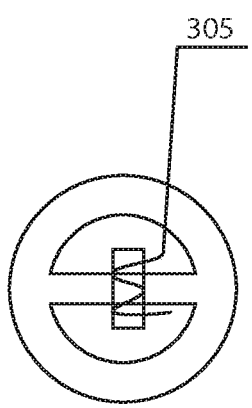
FIG. 11 is an end view of the atomizer shown in FIG. 10.

The atomizer (307) may be a capillary impregnation atomizer as in FIGS. 8 and 9, or a spray atomizer as in FIGS. 10 and 11. As shown in FIG. 4, the cigarette bottle assembly includes the cigarette liquid bottle (401), fiber (402) and suction nozzle (403). The fiber (402) containing cigarette liquid is located on one end of the cigarette liquid bottle (401). This end is inserted into the secondary shell (306) and lies against the atomizer (307). The suction nozzle (403) is located on the other end of the cigarette liquid bottle (401). Between the fiber (402) and interior wall of the cigarette liquid bottle (401) is an air intake hole (503).

Figure 5A:
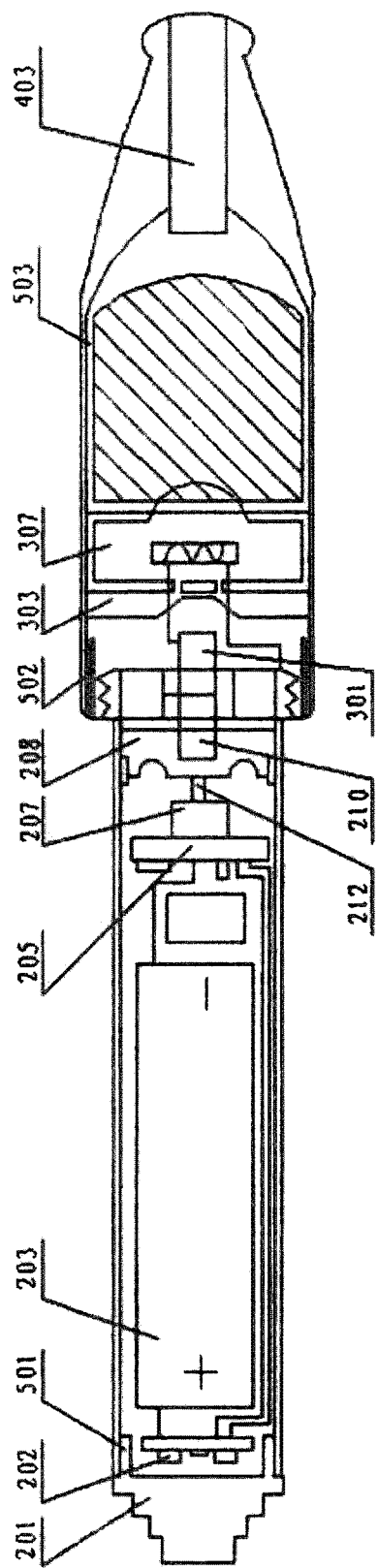
FIG. 5A is a section view of an electronic cigarette.

As shown in FIG. 5A, the standby state has the fully charged battery assembly shown on FIG. 2A fastened onto the atomizer assembly shown on FIG. 3, which is then inserted into the cigarette bottle assembly shown in FIG. 4. When the user slightly sucks the suction nozzle (403), negative pressure forms on the silica gel corrugated membrane (208) through the air intake hole (503) and the primary and secondary negative pressure cavities (210, 301). The silica gel corrugated membrane (208), under the action of suction pressure difference, distorts to drive the switch spring (212) and sensor (207), thus switching MOSFET electric circuit board (205). At this moment, the indicators (202) are lit gradually; the lithium ion battery (203) electrifies the heating body (305) inside the atomizer (307) through MOSFET electric circuit board (205) as well as the internal and external thread electrodes (302, 209).

The heating body (305) inside the atomizer (307) produces heat. The fiber (402) inside the cigarette liquid bottle (401) contains cigarette liquid, which soaks the micro-porous ceramics (801) inside the atomizer through the fiber (402). The air enters through the air intake hole (502), passes through the run-through hole on the air-liquid separator (303), and helps to form air-liquid mixture in the spray nozzle (304) of the atomizer (307). The air-liquid mixture sprays onto the heating body (305), gets vaporized, and is quickly absorbed into the airflow and condensed into aerosol, which passes through the air intake hole (503) and suction nozzle (403) to form white mist type aerosol.

When suction stops, the switch spring (212) and sensor (207) are reset; the atomizer (307) stops working; the indicators (202) gradually die down. When the operation times reaches the pre-set value, the atomizer (307) provides a work delay of 5-20 seconds per time, so as to remove the micro-dirt accumulated on the heating body (305).

Besides the micro-porous ceramics, the liquid supply material of the atomizer (307) may also be foamed ceramics, micro-porous glass, foamed metal, stainless steel fiber felt, terylene fiber, nylon fiber, nitrile fiber, aramid fiber or hard porous plastics. The heating body (305) is made of the micro-porous ceramics on which nickel-chromium alloy wire, iron-chromium alloy wire, platinum wire, or other electro thermal materials are wound. Alternatively, it may be a porous component directly made of electrically conductive ceramics or PTC (Positive Temperature Coefficient) ceramics and associated with a sintered electrode. The surface of the heating body (305) is sintered into high-temperature glaze to fix the zeolite grains, which are made of natural zeolite, artificial non-organic micro-porous ceramics or aluminum oxide grains. The cigarette liquid bottle (401) and suction nozzle (403) in the cigarette bottle assembly are made of non-toxic plastic. The fiber (402) inside of them is made of polypropylene fiber or nylon fiber to absorb cigarette liquid. In the battery assembly, there is a fine hole (501) on the indicator cap (201) for balancing the pressure difference on both sides of the silica gel corrugated membrane (208).

The cigarette liquid contains 0.1-3.5% nicotine, 0.05-5% tobacco flavor, 0.1-3% organic acid, 0.1-0.5% stabilizer, and propanediol for the remaining.

The primary and secondary shells (211, 306) are made of stainless steel tube or copper alloy tube with baked-enamel coating of real cigarette color.

Figure 12:
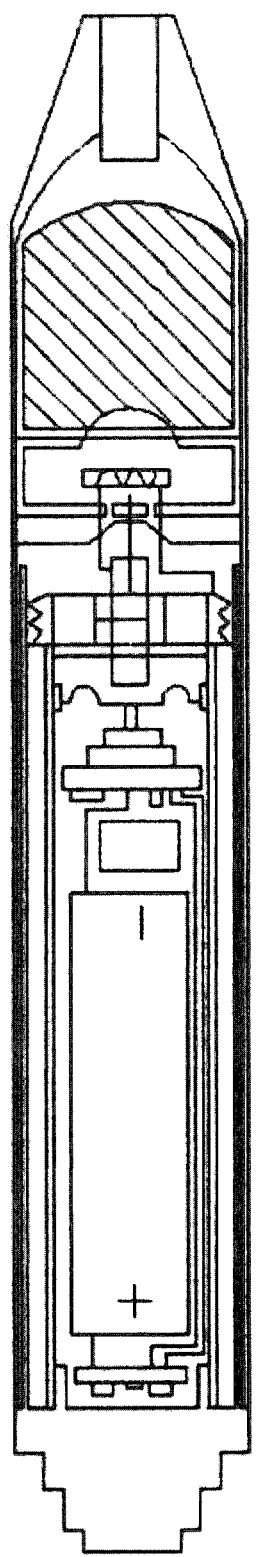
FIG. 12 is a section view of another embodiment.

As shown in FIG. 12, the diameter of the battery assembly may be increased in proportion, so that it is consistent with the diameter of the atomizer assembly. Its shell may be decorated with the leaf veins and sub-gloss brown-yellow baked-enamel coating, to create a cigar type device.

For charging the lithium ion battery (203), the screw thread electrode (601) matches the external thread electrode (209) on the battery assembly, so that it may be used as the charging interface.

Figure 2B:
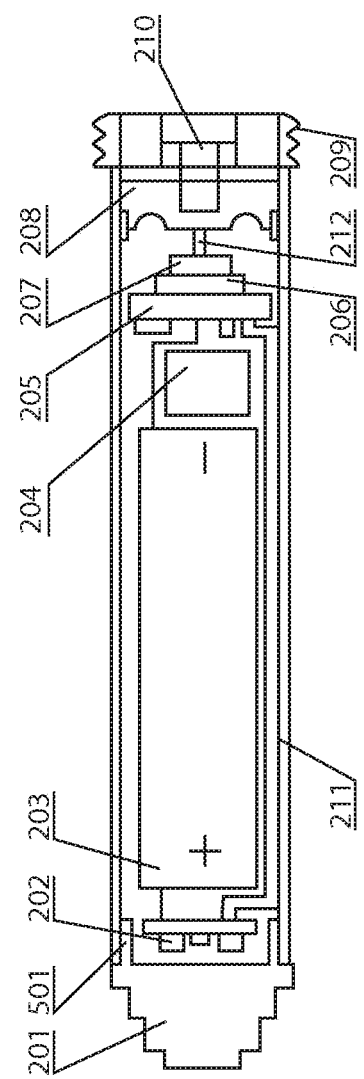
FIG. 2B is a view of another battery assembly.

The design in FIG. 2B is difference from the design in FIG. 1A as follows: Microcircuit (206) is added between MOSFET electric circuit board (205) and sensor (207). On the surface of the primary shell (211), there is a screen (204) for display of the power of the lithium ion battery (203) and the sucking times.

Figure 5B:
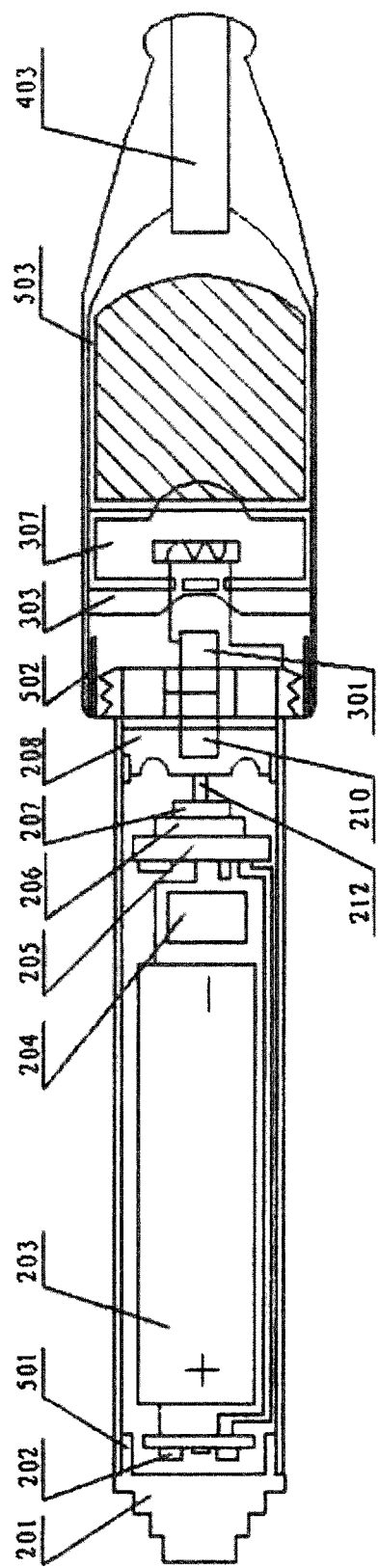
FIG. 5B is a section view of another embodiment.
Figure 6:
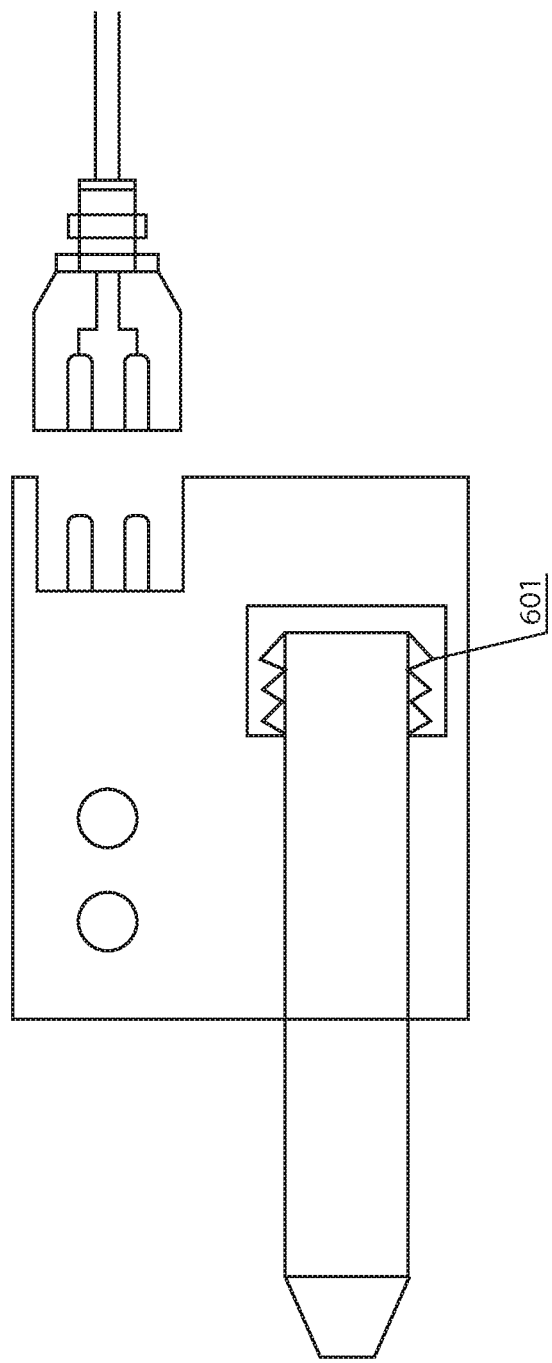
FIG. 6 is a diagram of a charger.

As shown in FIG. 5B, a fully charged battery assembly is attached onto the atomizer assembly, which is then inserted into the cigarette bottle assembly shown on FIG. 4. When the user slightly sucks the suction nozzle (403), negative pressure forms on the silica gel corrugated membrane (208) through the air intake hole (503) and the primary and secondary negative pressure cavities (210, 301). The silica gel corrugated membrane (208), under the action of suction pressure difference, distorts to drive the switch spring (212) and sensor (207), thus activating the Microcircuit (206) and MOSFET electric circuit board (205). At this moment, the indicators (202) are lit gradually; the lithium ion battery (203) electrifies the heating body (305) inside the atomizer (307) through MOSFET electric circuit board (205) as well as the internal and external thread electrodes (302, 209), so that the heating body (305) inside the atomizer (307) produces heat.

The fiber (402) inside the cigarette liquid bottle (401) contains cigarette liquid, which soaks the micro-porous ceramics (801) inside the atomizer through the fiber (402). The air enters through the air intake hole (502), passes through the run-through hole on the air-liquid separator (303), and helps to form air-liquid mixture in the spray nozzle (304) of the atomizer (307). The air-liquid mixture sprays onto the heating body (305), gets vaporized, and is quickly absorbed into the airflow and condensed into aerosol, which passes through the air intake hole (503) and suction nozzle (403) to form white mist type aerosol.

Figure 7:
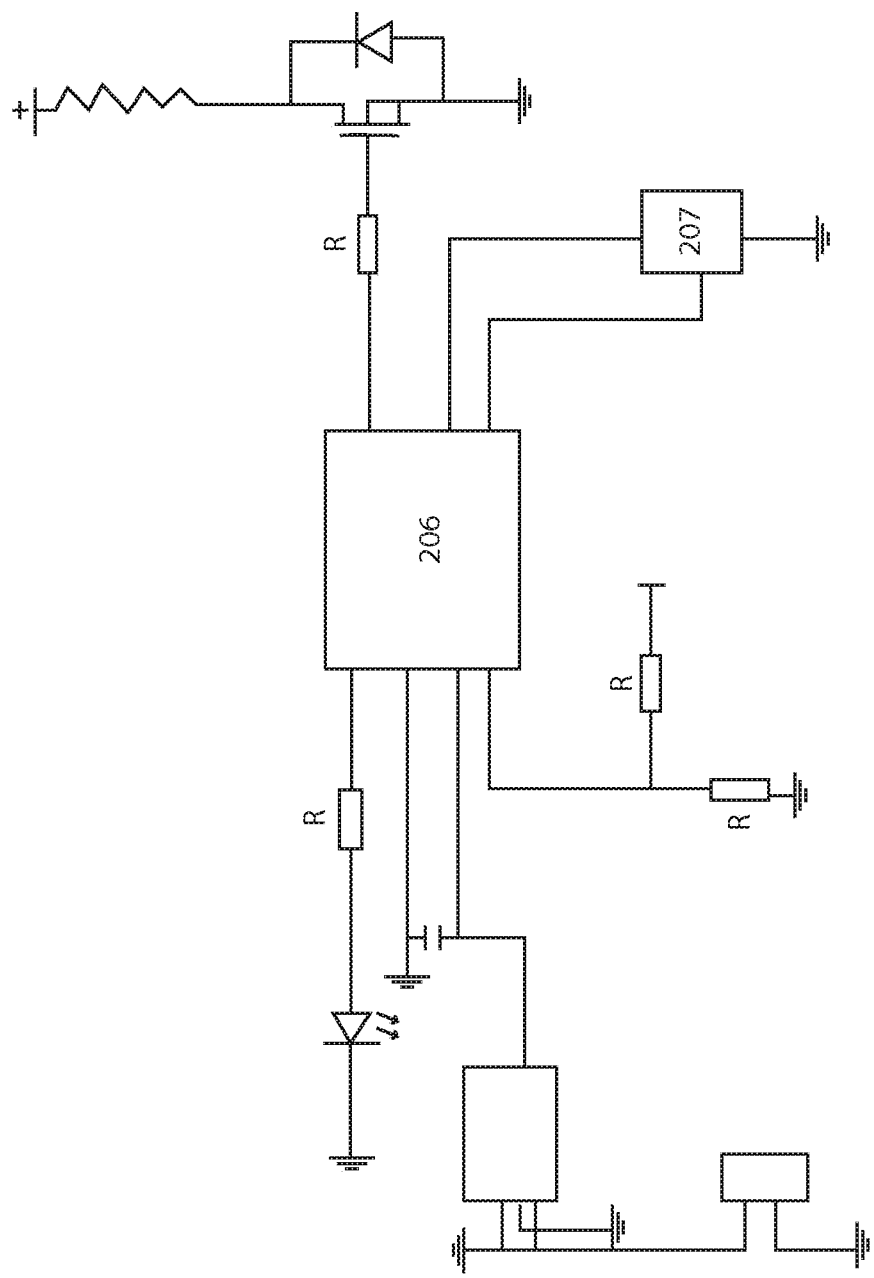
FIG. 7 is the electric circuit diagram.

As shown in FIG. 7, when the action of suction activates the sensor, Microcircuit (206) scans the sensor (207) in the power-saving mode of pulse, and according to the signal parameters of the sensor (207), restricts the atomizing capacity with the integral function of frequency to single operation time. Also, the microcircuit (206) accomplishes the pulse width modulation and over discharging protection for the constant power output, automatic cleansing for thousands of times per operation, step lighting/dying down control of the indicator, display of the operation times and battery capacity, automatic recovery after sensor malfunction shutdown, etc.

The unit and its connecting structure may also be loaded with drugs for delivery to the lung.

Above are just specifications of an example and do not necessarily restrict the scope of protection. Any equivalent modification made on the basis of the design spirit shall fall into the scope of protection.

I claim:

1. A vaporizing device comprising:
   a battery assembly comprising a battery assembly housing having a first end and a second end, with a battery electrically connected to a circuit board within the battery assembly housing;
   an indicator in the battery assembly housing electrically connected to the circuit board;
   a first electrode in the battery assembly housing;
   an atomizer assembly comprising:
   an atomizer assembly housing having a first end and a second end;
   a liquid supply in the atomizer assembly housing;
   a wire coil wound around a part of a porous body which is perpendicular to a longitudinal axis of the device;
   the porous body in contact with liquid from the liquid supply;

an airflow path in the atomizer assembly housing leading to an outlet;

a second electrode in the first end of the atomizer assembly housing;

the atomizer assembly engageable with the battery assembly to form the vaporizing device, with electricity conducted from the battery to the wire coil through the first and second electrodes for heating the wire coil.

2. The vaporizing device of claim 1 wherein the indicator comprises an LED.

3. The vaporizing device of claim 1 further including an air flow sensor electrically connected to the circuit board.

4. The vaporizing device of claim 1 with the porous body comprising a fiber material.

5. The vaporizing device of claim 4 with the porous body moving liquid to the wire coil by capillary action.

6. The vaporizing device of claim 1 further including a switch which switches the wire coil on and off.

7. The vaporizing device of claim 1 wherein the liquid supply comprises a plastic bottle containing the liquid and having a mouthpiece, with the outlet in the mouthpiece.

8. The vaporizing device of claim 1 with the liquid comprising 0.1-3.5% nicotine.

9. A vaporizing device comprising:
   a battery assembly comprising a battery, and an LED electrically connected to a circuit board within a battery assembly housing;
   a first electrode in an end of the battery assembly housing;
   an atomizer assembly comprising an atomizer in an atomizer assembly housing;
   the atomizer including a wire coil wound around a porous body, with the wire coil and the porous body positioned perpendicular to a longitudinal axis of the device, the porous body in contact with a supply of liquid;
   the wire coil and the porous body in an airflow path through the atomizer assembly housing leading to an outlet;
   wherein air passes across the wire coil and the porous body;
   a second electrode at an end of the atomizer assembly housing; and
   the battery assembly and the atomizer assembly electrically connected by engagement of the first electrode with the second electrode.

10. The vaporizing device of claim 9 further including an air flow sensor electrically connected to the circuit board.

11. The vaporizing device of claim 9 with the porous body comprising a fiber material.

12. The vaporizing device of claim 9 with the porous body moving liquid to the wire coil by capillary action.

13. The vaporizing device of claim 9 further including a switch which switches the wire coil on and off.

14. The vaporizing device of claim 9 wherein the supply of liquid comprises a plastic bottle containing liquid and having a mouthpiece, with the outlet in the mouthpiece.

15. The vaporizing device of claim 9 with the liquid comprising 0.1-3.5% nicotine.

16. A vaporizing device comprising:
   a battery assembly comprising a battery, an LED, and a micro-controller unit electrically connected to a circuit board within a battery assembly housing;
   a first electrode in an end of the battery assembly housing;
   an atomizer assembly comprising an atomizer in an atomizer assembly housing;
   the atomizer including a wire coil wound around a porous body, with the wire coil and the porous body positioned perpendicular to a longitudinal axis of the device, the porous body in contact with liquid contained in a plastic bottle having a mouthpiece;
   the wire coil and the porous body in an airflow path through the atomizer assembly housing leading to an outlet in the mouthpiece;
   wherein air passes across the wire coil and the porous body;
   an air flow sensor electrically connected to the circuit board;
   a second electrode at an end of the atomizer assembly housing; and
   the battery assembly and the atomizer assembly electrically connected by engagement of the first electrode with the second electrode, and with electricity conducted from the battery to the wire coil through the first and second electrodes.

\* \* \* \* \*